(12) United States Patent
Mercer et al.

(10) Patent No.: US 10,535,119 B2
(45) Date of Patent: *Jan. 14, 2020

(54) METHOD AND APPARATUS FOR ENHANCING 3D MODEL RESOLUTION

(71) Applicant: Intermap Technologies, Inc., Englewood, CO (US)

(72) Inventors: Nathan Zachary Mercer, Englewood, CO (US); Stephen Charles Griffiths, Englewood, CO (US); Michael John Wollersheim, Englewood, CO (US); Trevor Roy Miller, Englewood, CO (US); Qiaoping Zhang, Englewood, CO (US)

(73) Assignee: Intermap Technologies Inc., Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/398,027

(22) Filed: Apr. 29, 2019

(65) Prior Publication Data
US 2019/0311461 A1    Oct. 10, 2019

Related U.S. Application Data

(63) Continuation of application No. 16/221,859, filed on Dec. 17, 2018, now Pat. No. 10,325,349, which is a
(Continued)

(51) Int. Cl.
*G06T 3/40* (2006.01)
*G06T 5/10* (2006.01)
(Continued)

(52) U.S. Cl.
CPC .............. *G06T 3/40* (2013.01); *A61B 6/5258* (2013.01); *G06T 3/4053* (2013.01); *G06T 5/002* (2013.01);
(Continued)

(58) Field of Classification Search
CPC ........... G06T 3/40; G06T 5/002; G06T 5/003; G06T 5/007; G06T 5/004; G06T 5/10;
(Continued)

(56) References Cited

U.S. PATENT DOCUMENTS 5,109,430 A    4/1992   Nishihara
5,187,754 A    2/1993   Currin
(Continued)

FOREIGN PATENT DOCUMENTS

WO      2008034465 A1    3/2008
WO      2010056643 A2    5/2010

OTHER PUBLICATIONS

Non-Final Office Action in U.S. Appl. No. 14/825,806, dated Dec. 1, 2017, 13 pages.
(Continued)

*Primary Examiner* — Manav Seth
(74) *Attorney, Agent, or Firm* — Perkins Coie LLP

(57) ABSTRACT

Systems and methods of enhancing the resolution of digital terrain models (DTM) for location-based applications and analyses. The DTM enhancement process takes the signature of the input image (e.g., via the input image and a noise surface file with similar characteristics as the sensor used to capture the input image) and applies it to the DTM without including large features such as buildings. The disclosed methods include utilize a process similar to that used for enhancing a DSM based on mapping the changing intensity from the image file to changes in elevation in the DSM using a regression over a local neighborhood of pixels. Further, the disclosed methods do not rely on information about the sensors and are extendable to be able to utilize any types of images. Additionally, the disclosed embodiments are sensor agnostic and can be applied on any type of image collected by any type of sensor.

20 Claims, 23 Drawing Sheets

Related U.S. Application Data continuation-in-part of application No. 15/963,937, filed on Apr. 26, 2018, now Pat. No. 10,186,015, which is a continuation of application No. 15/723,154, filed on Oct. 2, 2017, now Pat. No. 10,002,407.

(60) Provisional application No. 62/544,608, filed on Aug. 11, 2017.

(51) Int. Cl.
| | | |
|---|---|---|
| *G06T 17/05* | (2011.01) | |
| *G06T 5/50* | (2006.01) | |
| *A61B 6/00* | (2006.01) | |
| *G06T 5/00* | (2006.01) | |

(52) U.S. Cl.
CPC ............... *G06T 5/007* (2013.01); *G06T 5/10* (2013.01); *G06T 5/50* (2013.01); *G06T 17/05* (2013.01); *G06T 2207/10044* (2013.01); *G06T 2207/20032* (2013.01); *G06T 2207/20182* (2013.01); *G06T 2207/20216* (2013.01); *G06T 2207/20224* (2013.01)

(58) Field of Classification Search
CPC . G06T 5/50; G06T 17/05; G06T 2207/10044; G06T 2207/20024; G06T 3/4053; G06T 7/73; G06T 2207/20032; G06T 2207/20182; G06T 2207/20216; G06T 2207/20224; A61B 6/5258; A61B 5/0064; G06K 9/46
See application file for complete search history.

(56) References Cited

U.S. PATENT DOCUMENTS

| | | | |
|---|---|---|---|
| 5,926,581 | A | 7/1999 | Pritt |
| 6,272,448 | B1 * | 8/2001 | Ishii .................. G06T 17/05 342/191 |
| 6,448,544 | B1 | 9/2002 | Stanton |
| 6,792,684 | B1 | 9/2004 | Hyyppa |
| 6,937,775 | B2 | 8/2005 | Gindele |
| 6,973,218 | B2 | 12/2005 | Alderson |
| 6,978,050 | B2 | 12/2005 | Hunter |
| 7,043,090 | B2 | 5/2006 | Gindele |
| 7,116,838 | B2 | 10/2006 | Gindele |
| 7,187,452 | B2 | 3/2007 | Jupp |
| 7,236,649 | B2 | 6/2007 | Fenney |
| 7,386,164 | B2 * | 6/2008 | Shragai .................. G06K 9/0063 382/154 |
| 7,627,491 | B2 | 12/2009 | Feyen |
| 7,639,842 | B2 | 12/2009 | Kelle |
| 7,856,312 | B2 | 12/2010 | Coombes |
| 7,881,913 | B2 | 2/2011 | O'Neil |
| 7,917,292 | B1 | 3/2011 | Du |
| 7,917,346 | B2 | 3/2011 | Sullivan |
| 8,010,294 | B2 | 8/2011 | Dorn |
| 8,139,111 | B2 | 3/2012 | Oldroyd |
| 8,239,179 | B2 | 8/2012 | Duncan |
| 8,295,554 | B2 * | 10/2012 | Francini .................. G06T 17/05 382/109 |
| 8,369,579 | B2 | 2/2013 | Barnes |
| 8,473,264 | B2 | 6/2013 | Frigerio |
| 8,655,595 | B1 | 2/2014 | Green et al. |
| 8,825,456 | B2 | 9/2014 | Vasudevan |
| 8,855,439 | B2 | 10/2014 | Louis |
| 8,874,187 | B2 | 10/2014 | Thomson |
| 9,147,285 | B2 | 9/2015 | Kunath |
| 9,299,191 | B2 | 3/2016 | Sinram |
| 9,830,690 | B2 | 11/2017 | Chiang |
| 9,875,554 | B2 | 1/2018 | Imber |
| 10,002,407 | B1 | 6/2018 | Mercer |
| 10,147,057 | B2 | 12/2018 | Zhang |
| 10,186,015 | B1 | 1/2019 | Mercer |
| 10,204,454 | B2 * | 2/2019 | Goldman .................. G06T 7/344 |
| 2003/0138152 | A1 | 7/2003 | Fennye |
| 2004/0260471 | A1 | 12/2004 | McDermott |
| 2008/0260237 | A1 * | 10/2008 | Savolainen .......... G06K 9/0063 382/154 |
| 2010/0292973 | A1 | 11/2010 | Barnes |
| 2011/0246935 | A1 | 10/2011 | Maeder |
| 2011/0295575 | A1 | 12/2011 | Levine et al. |
| 2012/0330553 | A1 | 12/2012 | Mollaei |
| 2013/0046471 | A1 | 2/2013 | Rahmes |
| 2013/0197807 | A1 | 8/2013 | Du |
| 2013/0342736 | A1 | 12/2013 | Numata |
| 2014/0267250 | A1 | 9/2014 | Tennant |
| 2015/0046139 | A1 | 2/2015 | Iwamura |
| 2015/0154805 | A1 | 6/2015 | Hsu |
| 2016/0148347 | A1 | 5/2016 | Guido |
| 2017/0358067 | A1 | 12/2017 | Jung |

OTHER PUBLICATIONS

Non-Final Office Action in U.S. Appl. No. 15/963,937, dated May 31, 2018, 10 pages.
Notice of Allowance in U.S. Appl. No. 14/825,806, dated Jul. 11, 2018, 12 pages.
Notice of Allowance in U.S. Appl. No. 14/825,806, dated Sep. 4, 2018, 11 pages.
Notice of Allowance in U.S. Appl. No. 15/723,154, dated Jan. 26, 2018, 9 pages.
Notice of Allowance in U.S. Appl. No. 15/963,937, dated Sep. 19, 2018, 8 pages.
Notice of Allowance in U.S. Appl. No. 16/221,859, dated Jan. 29, 2019, 10 pages.

* cited by examiner

|     |     |     |     |     |
|-----|-----|-----|-----|-----|
| 123 | 124 | 123 | 125 | 129 |
| 123 | 123 | 122 | 125 | 126 |
| 120 | 122 | 123 | 124 | 127 |
| 119 | 120 | 121 | 120 | 122 |
| 118 | 119 | 120 | 120 | 120 |

*FIG. 2A*

|    |    |    |    |    |
|----|----|----|----|----|
| 18 | 18 | 15 | 20 | 22 |
| 20 | 20 | 17 | 18 | 21 |
| 18 | 17 | 18 | 21 | 20 |
| 15 | 13 | 14 | 16 | 16 |
| 11 | 13 | 14 | 13 | 15 |

*FIG. 2B*

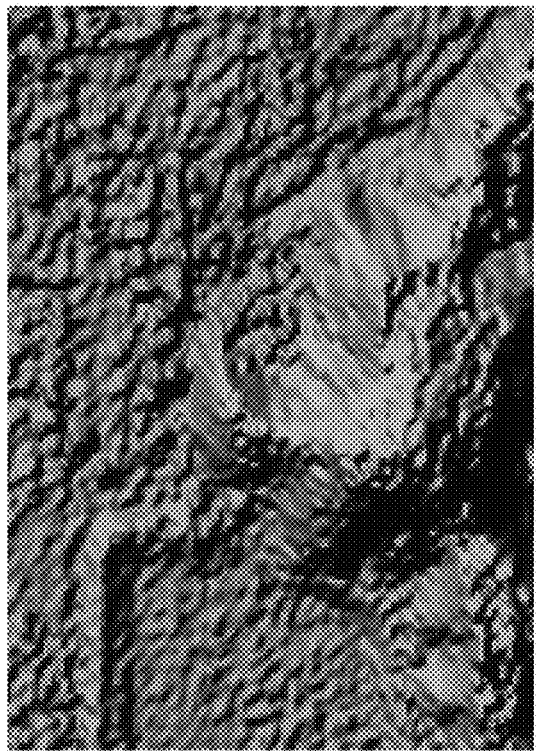
FIG. 10B (Source DSM associated with image)
FIG. 10A (Image)
FIG. 10C (Enhanced DSM, e.g., using method in FIG. 9)

FIG. 11B (DTM Resampled)
FIG. 11A (Input DTM)
FIG. 11C (DTM Resampled and Smoothed)

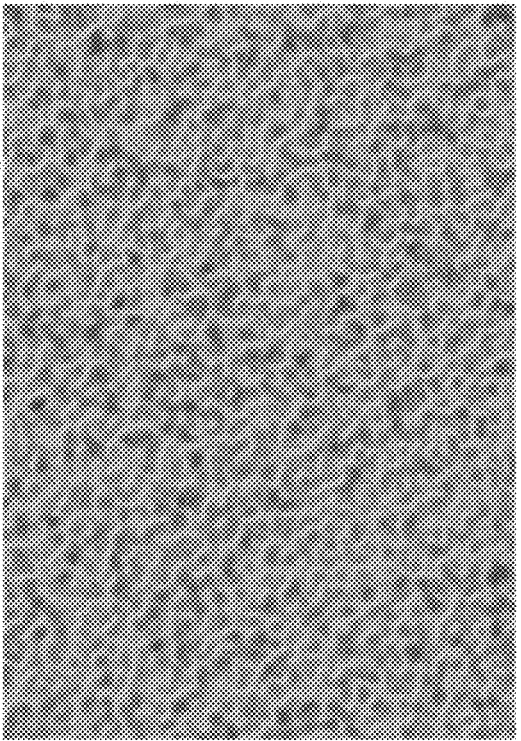
FIG. 12B (Noise Resampled)
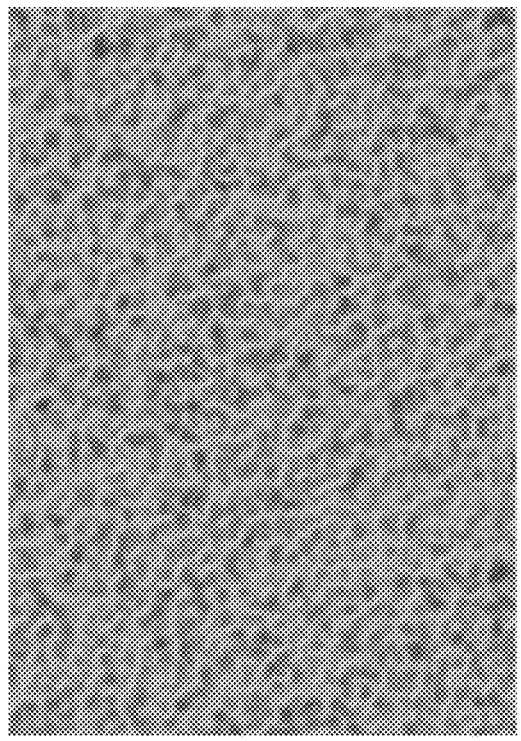
FIG. 12C (Noise Resampled and Smoothed)
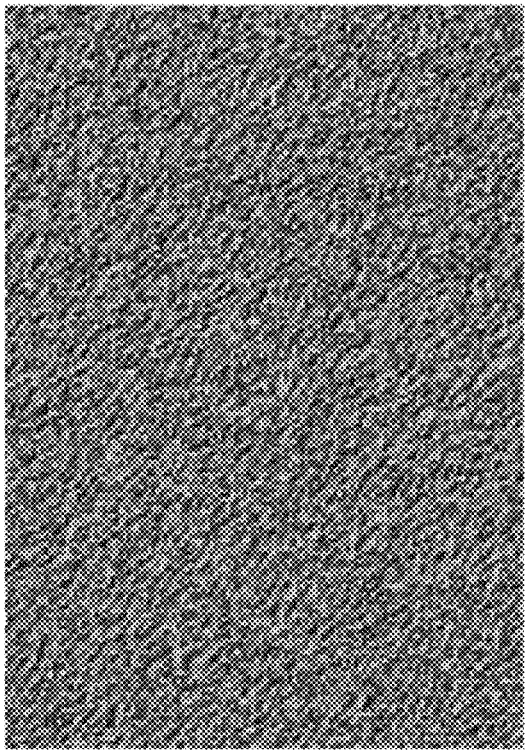
FIG. 12A (Input Noise)

*FIG. 13A (Enhanced Noise e.g., using method in FIG. 9)*
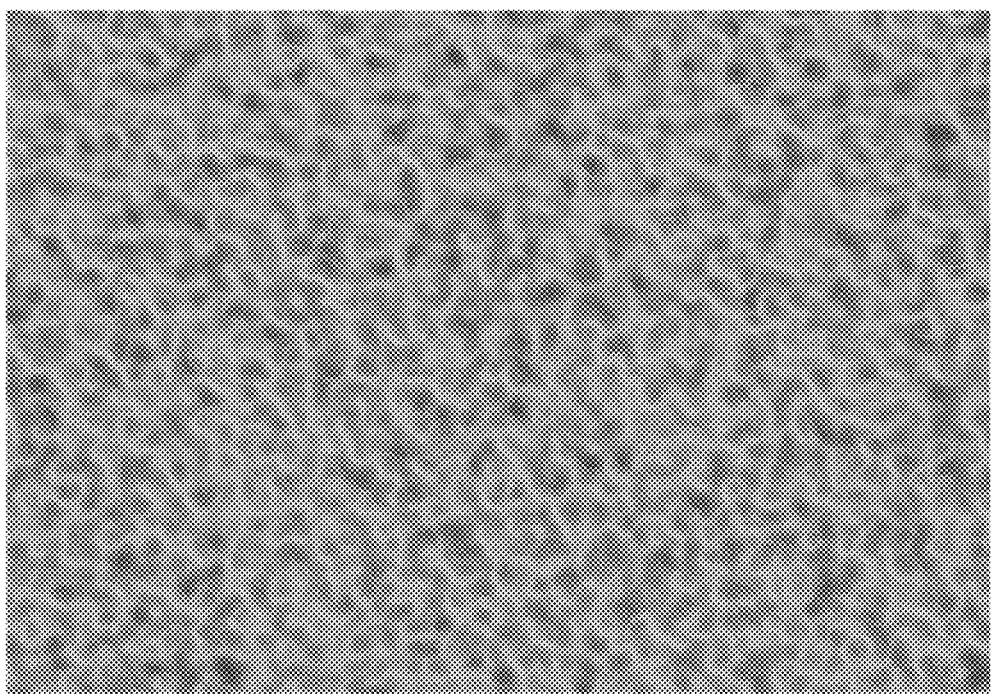
*FIG. 13B (Final Output – Enhanced DTM)*
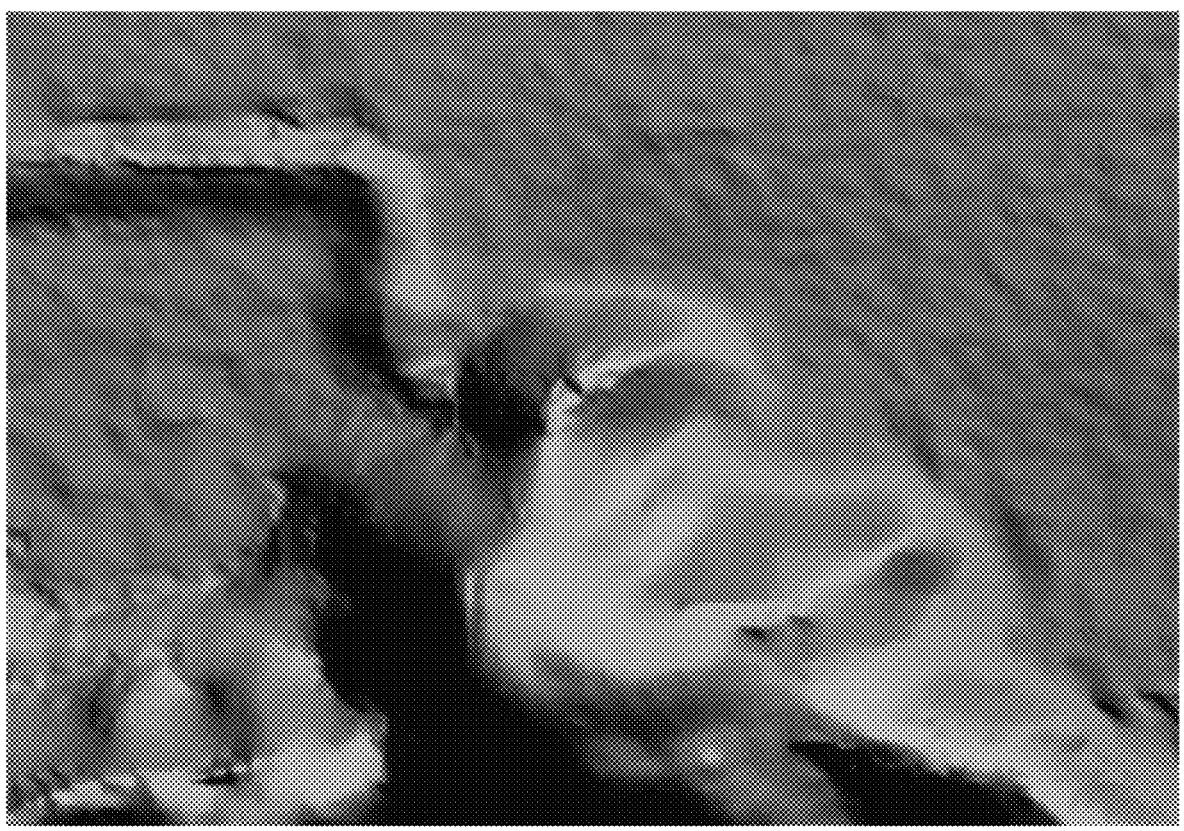

FIG. 15 (Obstruction Mask)

FIG. 16 (Enhanced DSM blended into DTM using Obstruction Mask)

METHOD AND APPARATUS FOR ENHANCING 3D MODEL RESOLUTION

CROSS-REFERENCE TO RELATED APPLICATIONS

This application is a continuation of U.S. patent application Ser. No. 16/221,859, filed Dec. 17, 2018, entitled "METHOD AND APPARATUS FOR ENHANCING 3D MODEL RESOLUTION," which is a continuation-in-part of U.S. patent application Ser. No. 15/963,937, filed Apr. 26, 2018, entitled "METHOD AND APPARATUS FOR ENHANCING 3D MODEL RESOLUTION," which is a continuation of U.S. Pat. No. 10,002,407 issued on Jun. 19, 2018, and entitled "METHOD AND APPARATUS FOR ENHANCING 30 MODEL RESOLUTION," which claims the benefit of U.S. Provisional Patent Application Ser. No. 62/544,608, filed on Aug. 11, 2017, and entitled "METHOD AND APPARATUS FOR ENHANCING 30 MODEL RESOLUTION," the disclosures of which are hereby incorporated by reference in their entireties.

TECHNICAL FIELD

This disclosure is related to modeling geospatial data. More particularly, the embodiments disclosed herein are directed at enhancing the resolution of geospatial data for location-based applications and analyses.

BACKGROUND

Radar-derived raster digital surface models (DSMs) provide a critical component for many modern applications, including flood risk analysis, telecommunications, pipeline routing, military, agriculture, and others. Interferometric Synthetic Aperture Radar (IFSAR) technologies have historically been able to produce DSMs with resolutions that range from 30 m up to 5 m depending on the sensor design and the operational parameters.

Noise gets introduced to the DSM when the DSM is processed at the same resolution as the image(s) from which the DSM is derived. The noise reduces the vertical accuracy of the data and can obscure spatial features that would otherwise be detectable. To address this issue, filtering is normally applied. However, filtering typically reduces the noise level at the expense of DSM resolution. This results in the DSM being generated at a lower resolution than the original images, e.g., as much as 4-8 times lower resolution than the image. Accordingly, there is a need for methods to recover the DSM resolution that gets lost due to filtering of the noise.

BRIEF DESCRIPTION OF THE DRAWINGS

FIG. 2A shows a sample neighborhood kernel associated with surface feature elevations.

FIG. 2B shows image gray values corresponding to the surface feature elevations of FIG. 2A.

FIG. 10A shows a representative optical image at 1 m resolution.

FIG. 10B shows a source DSM (at a native 5 m resolution) associated with the image of FIG. 10A.

FIG. 10C shows an enhanced DSM (at a 1 m resolution) associated with the image of FIG. 10A.

FIG. 11A shows an input DTM (at a native 5 m resolution) associated with the image of FIG. 10A.

FIG. 11B shows a resampled version of the input DTM of FIG. 11A.

FIG. 11C shows a resampled and smoothed version of the input DTM of FIG. 11A.

FIG. 12A shows a noise surface file representative of noise characteristics of a sensor used to capture the image of FIG. 10A.

FIG. 12B shows a resampled version of the noise surface file of FIG. 12A.

FIG. 12C shows a resampled and smoothed version of the noise surface file of FIG. 12A.

FIG. 13A shows an enhanced noise surface file associated with the noise surface file of FIG. 12A.

FIG. 13B shows the enhanced DTM (at an output resolution of 1 m) associated with the input DTM of FIG. 11A.

DETAILED DESCRIPTION

Figure 1A:
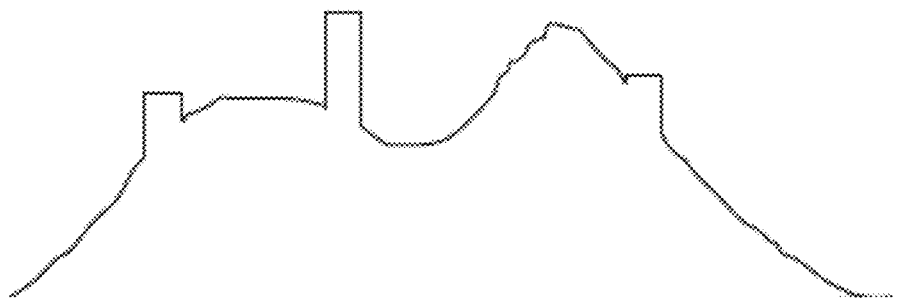
FIG. 1A shows a diagrammatic example of a DSM surface.

This disclosure is directed at systems and methods of enhancing or restoring details associated with high resolution images into a filtered DSM. The disclosed methods include mapping the changing gray scale values (intensity)

from the images to changes in elevation in the DSM using a regression over a local neighborhood of pixels. Further, the disclosed methods do not rely on information about the radar illumination geometry and are extendable to be able to utilize any types of images (e.g. optical images). Although, the present discussions are couched using examples of IFSAR DSMs and images, the technique is generalizable to include DSMs and images from any source and any resolution scale. Additionally, since the present methods do not attempt to reconstruct a surface normal vector, the performance of the methods in enhancing resolution of the DSMs are similar regardless of terrain slope.

The disclosed method takes a model (e.g., a DSM) as input and improves the spatial content and resolution using an image that includes more features than those included in the model. The method is applicable to DEMs and images generated from any sensor technology, including but not limited to IFSAR. Further, the disclosed methods are not dependent on the resolution scale of the input model. The methods can be applied to models of any resolution scale, using imagery of any resolution scale, when the imagery includes features that are not evident in the model. Additionally, the disclosed embodiments are sensor agnostic. That is, the disclosed methods can be applied on any type of images collected by any type of sensor. Examples of image types can be a thermal image, a multi-spectral image, a hyper-spectral image, an optical image, a medical image, a radar image, a weather image, a fused image from multiple types of sensors, a color image, a gray scale image, or a LiDAR intensity image, or any image spatially referenced to the DSM associated with the disclosed methods.

In some embodiments, shape-from-shading (SFS) methodologies are used to extract higher resolution information from images and translate such information into improved terrain definition in the elevation data. Conventional SFS methodologies are based on advanced knowledge about radar image phenomenology in order to properly utilize the radar geometry. These methods, however, are affected by common radar imaging phenomena like speckle, foreshortening and layover. Such phenomena can introduce undesirable artifacts or changes in the gray values of images. These methodologies are also very specific to the sensor technology being used. For example, shape-from-shading techniques for radar imaging are very different than they are for optical imaging, and both are dependent on sensor characteristics and imaging geometry. Furthermore, shape-from-shading techniques exploit variations in the image gray values to reconstruct a normal vector to the DSM surface at each image location, which although useful for accentuating changes in sloped areas, do not offer significant enhancement in flat terrain.

In some embodiments, the disclosed methods are applied to images contemporaneously when the DSM is generated. In some embodiments, errors between the geo-registration quality of the DSM and the images are avoided or minimized. Avoiding or minimizing the errors results in avoiding undesirable spatial features to be added at incorrect locations in the DSM.

IFSAR systems use two antennae separated by an interferometric baseline (B) to image the earth's surface by transmitting radar pulses toward the terrain. The reflected energy is recorded by both antennae, simultaneously providing the system with two SAR images that include amplitude and phase of the same point on the ground, with the two images being separated only by the phase difference created by the space between the two antennae. In addition, as the aircraft passes over the terrain, global positioning system (GPS) data from both aircraft- and ground-based GPS devices as well as navigation data from an inertial measurement unit (IMU) onboard the aircraft can be collected. This navigation data is processed to provide the precise position of the aircraft.

The phase difference between the antennae for each image point, along with range, baseline, GPS, and navigation data, is used to infer the precise topographic height of the terrain being imaged. This enables the creation of an interferogram (depicting the phase difference) from which the DSMs can be derived. Through additional processing, the disclosed DTM is generated.

The DSM is a topographic model of the earth's surface that can be manipulated using a computer. Surface elevation models play a critical role in applications such as biomass studies, flood analysis, geologic and topographic mapping, environmental hazard assessment, oil and gas, telecommunications, and many other applications. The DSM includes elevation measurements that are laid out on a grid. These measurements are derived from the return signals received by two radar antennae mounted on an aircraft. The signals bounce back from first surface they strike, making the DSM a representation of any object large enough to be resolved, including buildings and roads, as well as vegetation and other natural terrain features.

As technologies advance, the demand for higher resolution DSMs that can meet the specifications of modern applications is rising. In such instances where high accuracy and densely sampled elevation data are desirable objectives, other technologies such as Light Detection and Ranging (LIDAR) and stereo photogrammetry can be employed. However, the costs associated with utilizing these technologies can be prohibitive. The higher cost places a limitation on the extent of data that can practically be acquired. For example, in some situations, the dataset can be limited to a smaller size. When compared against these technologies, in some instances, IFSAR can be a more efficient and economical data collection platform since IFSAR is able to penetrate through cloud, smoke, fog and haze and can collect wider swaths of data by aircraft flying at higher altitudes, yielding greater ground coverage.

Preparing Input

In some embodiments, the disclosed method is based on the raster DSM pixels being coincident with the image pixels. Thus, the first step is that the DSM is resampled so that for every image pixel, there is a corresponding DSM pixel. The resampling can be done using techniques such as bilinear resampling, bicubic resampling, nearest neighbor resampling, natural neighbor resampling, kriging resampling, box average resampling, or box median resampling. In some embodiments, the images for input are in grayscale format with a single intensity value for each pixel. Therefore, if a color optical image is being used, the color image is first converted into a grayscale format.

Isolating Surface Features

Low frequency terrain variations typically have a negative impact on the results because the algorithm maps localized changes in elevation to the image grayscale changes. According to disclosed embodiments, slopes present in the terrain are interpreted as elevation change(s), but are not related to the localized distinguishable grayscale changes in the image. Therefore, these slopes are removed to eliminate this confounding effect and isolate the surface feature elevations.

There are many possible ways to identify the low frequency terrain variations. In some embodiments, low frequency terrain variations are identified by applying a coarse smoothing operation to the DSM. The specific parameters of a smoothing filter (e.g., an averaging filter or a median filter) are selected so that the surface features are removed without over-smoothing the actual terrain. For example, over-smoothing can be prevented by ensuring the filter width is not too large. That is, the filter width is chosen to be large enough to remove the surface features, but no so large that it causes the over smoothing of the terrain. When a smoothing filter is applied to the DSM, the size of the filter is defined typically by the number of raster pixels included in the filter kernel. For example, if a DSM has pixels that are 5 meters wide, and a 5×5 smoothing filter is applied, the filter may have a size of 25 m×25 m. This size of kernel can be effective at smoothing over features that are smaller than 25 m in size. Features larger than this may be smoothed to some degree, but not removed from the DSM. As a side-effect of this process, terrain definition can be reduced to some extent because sharp break and drain lines can be rounded off with a radius proportional to the smoothing filter size. When implementing the smoothing process, the area being operated on is analyzed to select a kernel larger than the largest surface feature that needs to be removed. As an example, if a particular area has buildings that are no larger than 18 m in length and in width, a 4×4 kernel size (20 m by 20 m based on 5 m pixels) may be effective at removing the surface features while preserving as much terrain definition as possible. If an area has buildings that are 47 m in length and in width, a larger filter can be used (10×10 kernel size for example).

Another approach is to use a Fourier domain filter to identify low-order terrain variations from the DSM and remove the high frequency content. Additional low frequency terrain identification algorithms can be used that may be more complex, but produce superior results. In some embodiments, a Digital Terrain Model (DTM) is used.

The DTM is a topographic model of the bare earth that can be manipulated using a computer. Vegetation, buildings, and other cultural features have been digitally removed from the DTM, leaving just the underlying terrain. (A DTM is created by removing vegetation, buildings, and other cultural features from a DSM. This is achieved using the disclosed methods, according to which terrain elevations are derived from measurements of bare ground included in the original radar data as well as by manually reviewing and editing every pixel. One key feature of a DTM is that the DTM infers the terrain characteristics that may be hidden in the DSM.

Figure 1B:
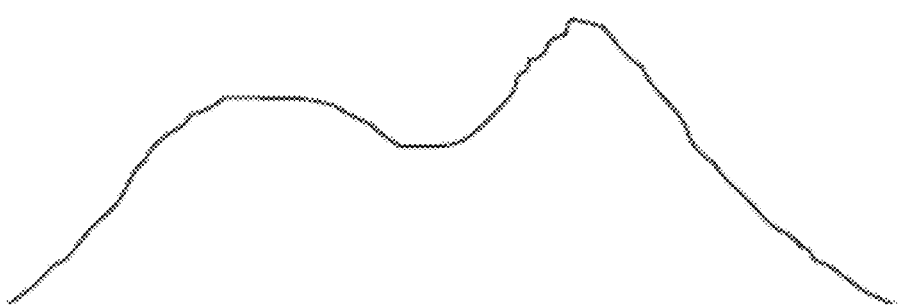
FIG. 1B shows a diagrammatic example of low frequency terrain included in the DSM surface of FIG. 1A.
Figure 1C:
FIG. 1C shows diagrammatic examples of surface features from the DSM surface of FIG. 1A.

Regardless of how the low frequency terrain is obtained, the process of isolating the surface features is based on subtraction of the low frequency terrain from the DSM. The result is a difference surface that is typically flat except for noise and surface features. This process is illustrated in FIG. 1 and the equation describing the operation is given in Equation (1).

$$\Delta = DSM - T \qquad (1)$$

where:
$\Delta$ is the isolated surface features,
DSM denotes the upsampled DSM, and
T is the low frequency terrain.

Adjusting Surface Features

The process operates on the surface features ($\Delta$ from Equation (1)) and the grayscale image, iterating on a pixel-by-pixel basis. At each pixel, a correspondence table is constructed that provides a mapping of the difference values (e.g., $\Delta$ values) and the image values for all pixels in a neighborhood. The neighborhood size may vary.

FIG. 2a shows a sample neighborhood kernel associated with surface feature elevations included in a difference surface. In FIG. 2a, an example 5×5 kernel is used. The surface elevation values shown in FIG. 2a are multiplied by 100 simply for demonstration purposes, since these values are typically close to zero in a real application. The pixel at the center is an example pixel being operated on.

FIG. 2b shows image gray values corresponding to the surface feature elevations of FIG. 2a. Using the correspondence table of local elevation difference/image gray value pairs, in some embodiments, a linear least squares approach is used to fit a line to the values with the equation:

$$Y = mx + b \qquad (2)$$

where:
Y is the surface feature elevation ($\Delta$), (e.g., shown in FIG. 2a)
x is the image gray value, (e.g., shown in FIG. 2b)
m is the slope of the best-fit line, and
b is the y-intercept of the best-fit line.

Figure 3:
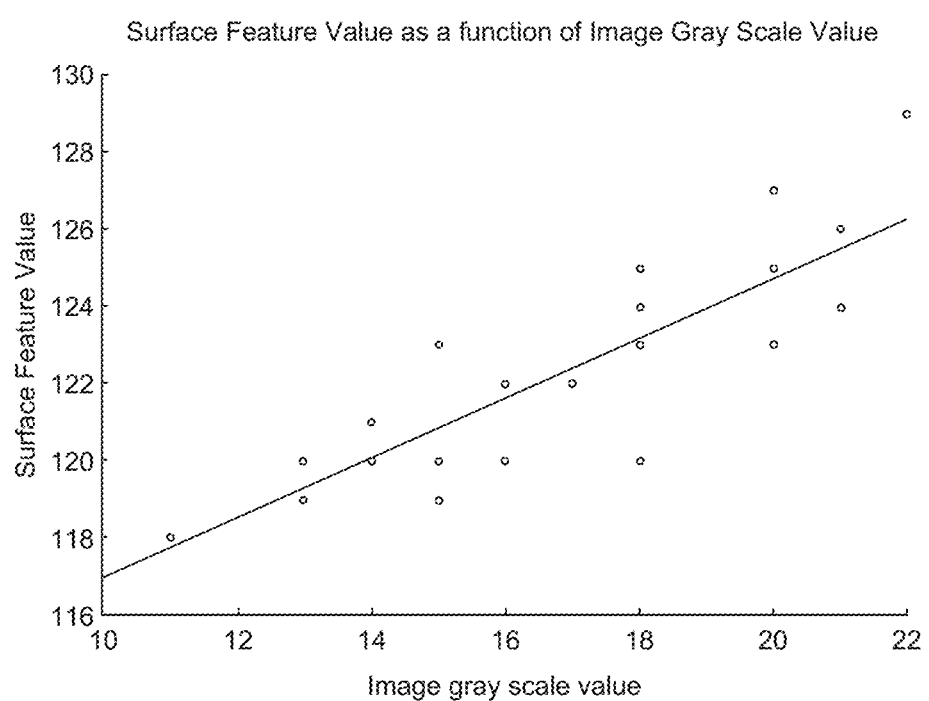
FIG. 3 depicts a line of best fit for the surface feature and gray scale values in FIG. 2a and FIG. 2b respectively.

Using the pixel neighborhood provides a set of points that can be used to determine the slope and intercept values for Equation (2). As an example, the 21×21 pixel neighborhood provides 441 points that can be used to determine the slope and intercept values for Equation (2). Upon determining the slope and intercept, the relationship for mapping gray values to elevation adjustment is established for the specific neighborhood of the target pixel. The adjusted elevation for the target pixel can be computed by applying Equation (2) to the gray value of the target pixel (at the center of the kernel). FIG. 3 depicts a scatter plot of the example values given from FIG. 2 and shows the best fit line to demonstrate how this works.

After all pixels are adjusted, these surface features are added back to the low frequency terrain surface. This produces the output DSM. According to disclosed embodiments, the output DSM is invariant to changes in one or more pixel values in the original image. A linear model described herein is for discussion purposes only. In some embodiments, the fit/regression model can be a non-linear model, e.g., a second order or a third order model. Further, the neighborhood kernel can be of any size.

Example Results

In some embodiments, the first model and the second model can be generated using a digital surface model (DSM), a weather model, a medical imaging/tomographic model, or a three dimensional (3D) digital model.

Figure 4:
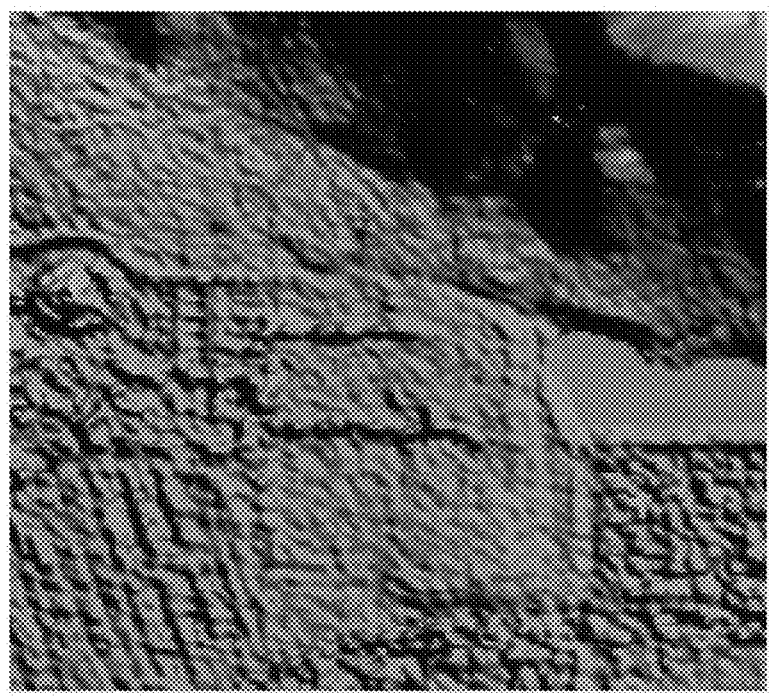
FIG. 4 shows an example input DSM at a native 5 m resolution.
Figure 5:
FIG. 5 shows a radar image at a native resolution of 1.25 m that is associated with the DSM shown in FIG. 4.
Figure 6:
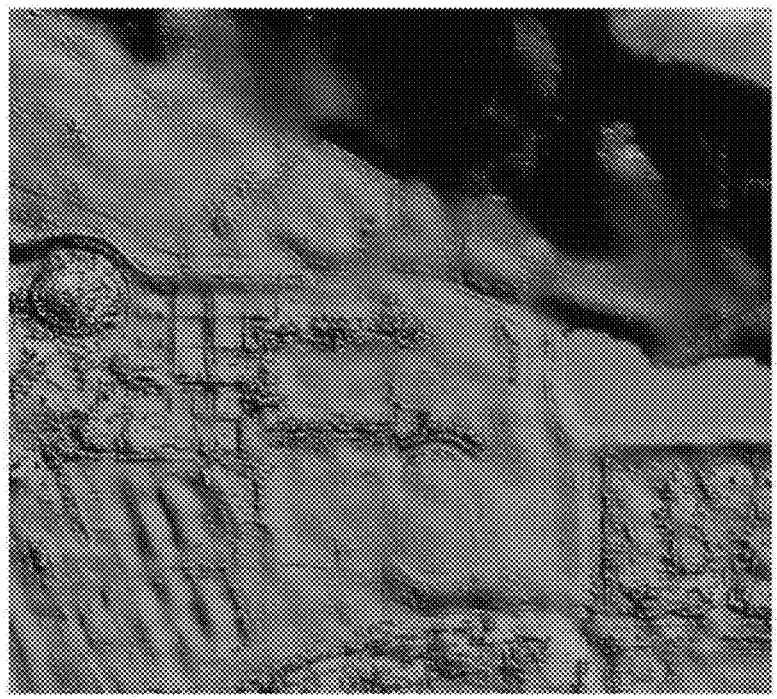
FIG. 6 shows an output DSM corresponding to the radar image shown in FIG. 5.

Results for a sample area are shown in FIGS. 4 through 8. FIG. 4 shows an input DSM at a 5 m resolution. The associated radar image is shown in FIG. 5, with a resolution of 1.25 m. The output DSM (shown in FIG. 6) is generated at 1.25 m resolution using a DTM to obtain the difference surface and a 21×21 kernel size. Comparing FIG. 4 with FIG. 6, it may be seen that details that were not represented in the input DSM in FIG. 4 are included in the output DSM in FIG. 6.

Figure 7:
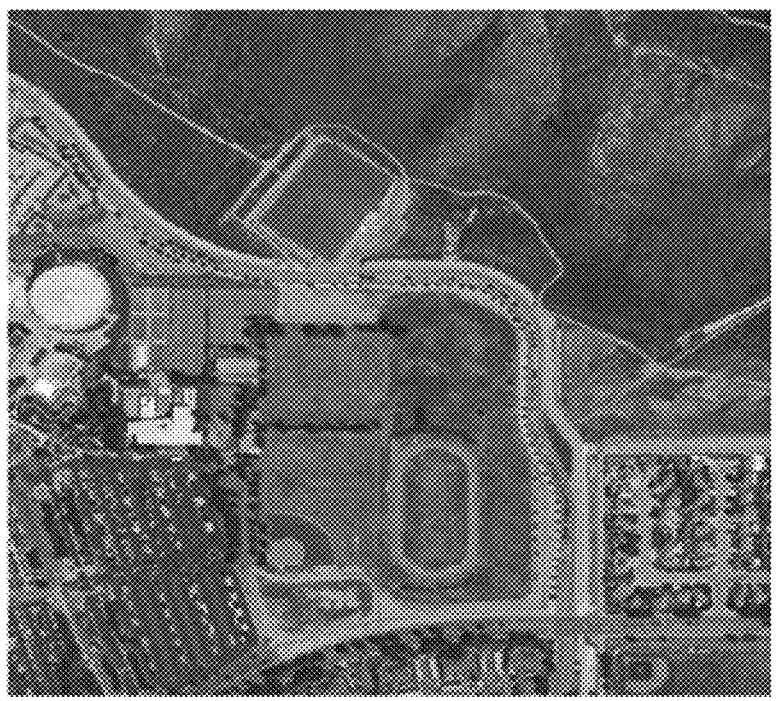
FIG. 7 shows an optical image corresponding to the geographical area of FIG. 5.
Figure 8:
FIG. 8 shows an output DSM corresponding to the optical image shown in FIG. 7.

To demonstrate the flexibility of the disclosed method, the method is applied to an optical image instead of a radar image. For example, FIG. 7 shows an optical image corresponding to the geographical area of FIG. 4. The optical image in FIG. 7 is at a 1.25 m resolution. FIG. 8 shows the resulting output DSM at 1.25 m resolution when the same parameters are used (DTM difference surface method, with 21×21 kernel size). The results show that the described methods work for both radar and optical images.

In some embodiments, the disclosed methods are applied using an iterative procedure for refining the model for a pre-specified number of iterations. In such embodiments, the second model is produced during the first iteration. The second model becomes the first model in the second iteration. In this iterative procedure, the first iteration can be based on a model that did not fully capture the feature content that was evident in the image. After applying the disclosed methods, the second model is an improvement to the first model and more accurately captures those features. As the iterative procedure continues, the model values move closer to the real values.

In some embodiments, the disclosed methods can be applied progressively, where resolution and feature content are added in stages. For example, the disclosed methods could be used to enhance a 10 m resolution DSM to 1.25 m either directly in one step, or progressively in stages. The stages could be to first enhance from 10 m to 5 m, then from 5 m to 2.5, and then from 2.5 m to 1.25 m, for example. In some applications, a progressive approach produces better results, such as when there is a large gap between the input model resolution and the output model resolution. The second model becomes the first model in the second step. In this progressive procedure, the first step can be based on a model that did not fully capture the feature content that was evident in the image. After applying the disclosed methods, the second model is an improvement to the first model and more accurately captures those features. As the progressive procedure continues, the resolution moves closer to the desired target resolution which is typically the full resolution of the input image (e.g. 1.25 m in this example).

Figure 9:
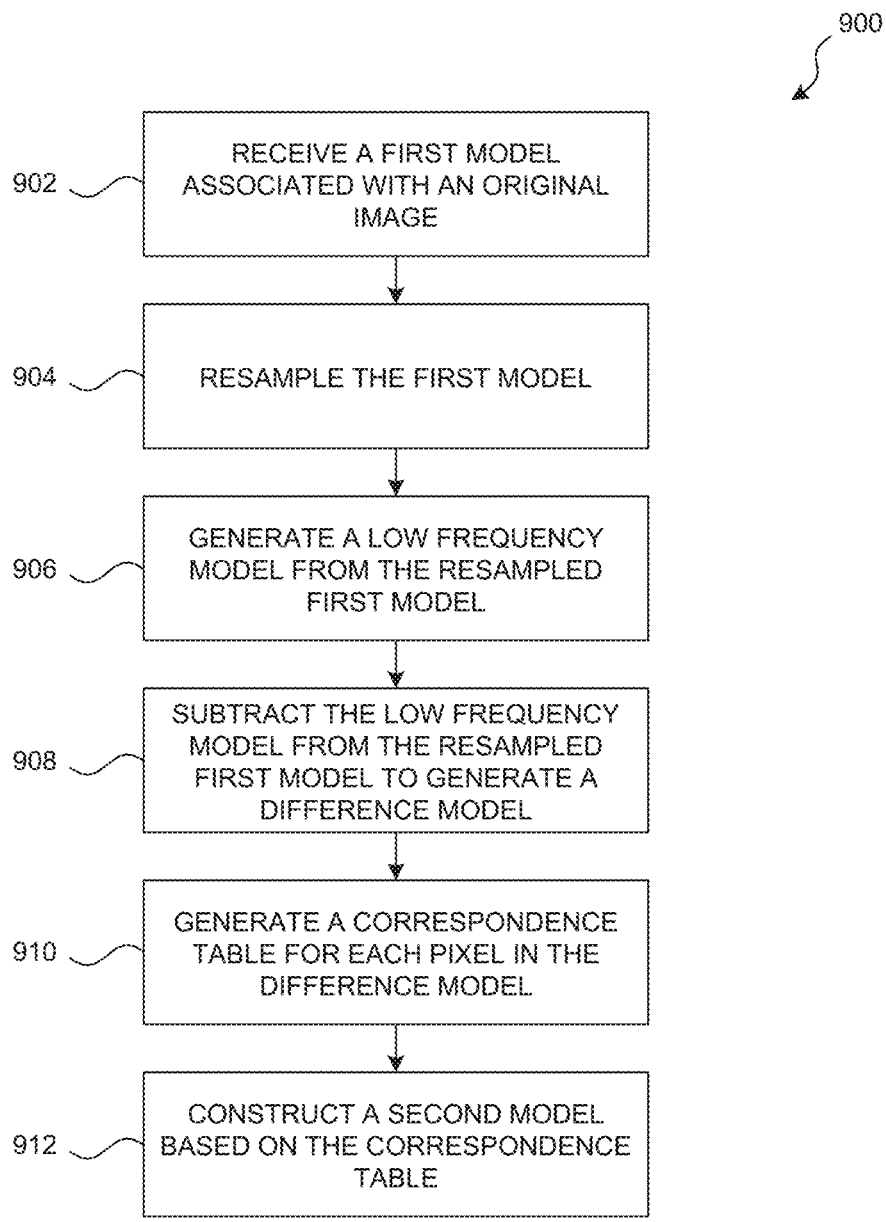
FIG. 9 shows steps of a flowchart associated with enhancing the resolution of geospatial data.

FIG. 9 shows steps of a flowchart associated with a process for enhancing the resolution of geospatial data. At step 902, the step receives a first model spatially referenced or associated with an original image. That is, in some embodiments, the original image used is spatially referenced to the model being enhanced. This implies that the location of each pixel in the image can be translated to a location on the model with a high degree of accuracy. Thus, the disclose methods are able to extract associations between image pixels to locations in the model, so that the image pixels can be used to enhance detail in the model. At step 904, the process resamples the pixels included in the first model. At step 906, the process generates a low frequency model from the resampled first model. At step 908, the process subtracts the low frequency model from the resampled first model for generating a difference surface model. At step 910, the process generates a correspondence table for pixels in the difference surface model by mapping pixels in the difference surface model to a group of pixels in the original image. In some embodiments, the group of pixels in the original image are included in a neighborhood adjacent to a pixel in the difference surface model. In some embodiments, the process extracts grayscale values for pixels. At step 912, the process constructs a second model by manipulating grayscale values of the pixels in the original image based on the correspondence table. According to disclosed embodiments, the resolution of the second model is invariant to scale changes in the original image or characteristics of sensors associated with capturing the original image. In some embodiments, the sensor characteristics can be related to the positioning method (for example, orbit model or kinematic positioning solution) of the platform on which the sensors are arranged. In some embodiments, sensor characteristics can be related to the knowledge of the remote sensing geometry (for example, interior and exterior orientation parameters for optical imaging, range-sphere and Doppler cone intersection for radargrammetry, antenna positioning for IFSAR, boresighting, and lever arm measurements for many sensor types). In some embodiments, sensor characteristics can be related to the electro-magnetic properties of the imagery produced by each sensor. For example, radar imagery may show variations in the imagery due to differing moisture content in the soil, whereas electro-optical imagery may show such variation. The methods disclosed herein are invariant to sensor characteristics.

This document discloses a new method for enhancing DSM resolution and spatial content by using detailed images to guide the resampling procedure. The method presented can be applied to optical or radar image inputs and performs consistently regardless of terrain slope. That is, the disclosed methods equally enhance the resolution of equally two identical features, even if one of those features is on highly sloped terrain, while the other is on flat terrain. In other words, the presence of slope(s) of the terrain has/have no effect on the performance of enhancement of the resolution of the features on the terrain. Additionally, the disclosed methods are easier to implement than traditional shape from shading techniques and can be applied to input DSM sources of any resolution scale.

The results (depicted in FIGS. 4-8) of applying the disclosed method demonstrate enhanced resolution in the output DSM with detailed feature content coming from the image that is not present in the input DSM. Resolution is increased at least by a factor of 4 in these cases, which is sufficient, e.g., for enabling applications that demand higher accuracy and more densely posted terrain information. The disclosed methods can also be applied for rapidly updating and improving existing DSMs without re-acquiring the elevation data.

Enhancing Resolutions of Digital Terrain Models (DTMs):

The DTM is a topographic model of the bare earth that can be manipulated using a computer. Vegetation, buildings, and other cultural features are not included in the DTM. Because a DTM primarily includes the underlying terrain, a DTM can be created by removing vegetation, buildings, and other cultural features from a DSM. A DTM can also be generated from classified multi-return LiDAR points.

The process of generating DTMs from DSMs often involves steps that can be destructive to the texture and definition of the terrain. For example, a smoothing process may be used to remove surface texture in vegetated and urban areas prior to shifting elevations down to the true ground level. Smoothing may also be used in transition zones to blend the boundary between previously obstructed areas and the surrounding bare earth terrain. Thus, a DTM infers the terrain characteristics that may be hidden in the DSM.

In another example, multi-return LiDAR points can be used to produce DTMs. In these examples, there may be a sparse availability of ground return points (e.g., a dense forest canopy may not reveal much of the underlying terrain hidden by the canopy). Alternatively, there may be no observable ground points, which occurs where buildings are located in a dense urban location (e.g., downtown New York City). When ground points are sparse, large area interpolation can be used to fill in the terrain elevation voids. However, these interpolated areas turn out to be overly smooth, artificial-looking, and devoid of the details and texture associated with natural terrains.

Embodiments of the present disclosure are directed at enhancing the resolution of DTMs. The resolution of the enhanced DTM is invariant to scale changes in the original image or the noise characteristics of the sensor used to capture the original image. The process for enhancing the resolution of a DTM approximates the noise characteristics of the sensor type used to produce the DTM. Non-limiting examples of sensors can be IFSAR, LiDAR, stereo photogrammetry, stereo SAR, or other suitable types of sensors for capturing images. The process further involves adding real terrain signatures from the images to restore the terrain data to the full definition (e.g., higher resolution) that is observed in the images.

FIG. 10A shows a representative optical image at a native resolution of 1 m. FIG. 10A is for illustrative purposed only. The disclosed technology is applicable to any type of images and not limited to optical images. Examples of image types can be a thermal image, a multi-spectral image, a hyperspectral image, an optical image, a medical image, a radar image, a weather image, a fused image from multiple types of sensors, a color image, a gray scale image, or a LiDAR intensity image, or any image spatially referenced to the DSM associated with the disclosed methods. Furthermore, the disclosed technology is applicable to images, DTMs, and DSMs at any resolution.

FIG. 10B shows a DSM associated with the image of FIG. 10A. The DSM of FIG. 10B is at a resolution of 5 m, i.e., the DSM is at a lower resolution than the image, which has a resolution of 1 m. Noise gets introduced to the DSM when the DSM is processed at the same resolution as the image(s) from which the DSM is derived. The noise reduces the vertical accuracy of the data and can obscure spatial features that would otherwise be detectable. As a result, the resolution of the DSM is lower than the resolution of the input image.

FIG. 10C shows an enhanced DSM (at a 1 m resolution) associated with the image of FIG. 10A. In some embodiments, the enhanced DSM is generated according to the method described in accordance with the flowchart of FIG. 9. That is, the method uses a correspondence table of local elevation difference/image gray value pairs, an enhanced DSM can be generated.

FIG. 11A shows an example DTM (at a native 5 m resolution) associated with the image of FIG. 10A. The DTM and the image are used as inputs to the process of DTM enhancement, with the output DTM having an enhanced resolution compared to the input DTM. DTM is created by removing vegetation, buildings, and other cultural features from a DSM.

FIG. 11B shows a resampled version of the input DTM of FIG. 11A. The resampled version can be created by interpolating the input DTM to the output resolution (e.g., 1 m). The input DTM is resampled so that for every image pixel, there is a corresponding pixel in the enhanced (output) DTM. For the resampled DTM in FIG. 11B, a bilinear resampling is done. In alternative embodiments, the resampling can be done using techniques such as bicubic resampling, nearest neighbor resampling, natural neighbor resampling, kriging resampling, box average resampling, or box median resampling.

FIG. 11C shows a resampled and smoothed version of the input DTM of FIG. 11A. That is, FIG. 11C is generated by smoothing the resampled DTM of FIG. 11B. In FIG. 11C, the resampled DTM is smoothed by applying a moving kernel average filter to reduce interpolation artefacts introduced during the resampling (e.g., discussed in FIG. 11B). The size of the kernel can correspond to the ratio of the input resolution (e.g., 5 m) and the final resolution (e.g., 1 m). Other smoothing techniques that may be applicable include additional kernel-based filters like Gaussian, Laplacian or median kernel filters, or low-pass Fourier domain techniques like Butterworth, Chebyshev or Bessel filters.

FIG. 12A shows a noise surface file representative of noise characteristics of a sensor used to capture the image of FIG. 10A. The noise surface file can be a computer-generated file representative of (or, emulating) the noise characteristics of the sensor used to capture the original image. The noise surface file of FIG. 12A is generated in two steps. In the first step, computer-generated using random numbers from a uniform distribution between −0.5 and 0.5. This noise surface file matches the noise characteristics of the sensor used to capture the input IFSAR DEM. In alternate embodiments, any suitable random number generator can be used to generate a noise surface file. In the second step, the computer-generated noise surface file is passed through a 1 sigma Gaussian smoothing filter. Typically, the choice of the smoothing filter emulates the noise characteristics of the sensor used to capture the original image. Other smoothing filters can be chosen for different types of sensors. Other smoothing techniques that may be applicable include additional kernel-based filters like Gaussian, Laplacian or median kernel filters, or low-pass Fourier domain techniques like Butterworth, Chebyshev or Bessel filters, as appropriate to best suit the sensor characteristics.

FIG. 12B shows a resampled version of the noise surface file of FIG. 12A. The resampling of the noise surface file is performed similarly to the DTM resampling discussed in connection with FIG. 11B. For example, the noise surface file (generated after the second step discussed in connection with FIG. 12A) is resampled using a bilinear resampling method.

FIG. 12C shows a resampled and smoothed version of the noise surface file of FIG. 12A. The smoothing of the resampled noise surface file (of FIG. 12B) is performed by passing the resampled noise surface file through a kernel average filter to reduce artefacts that may be introduced from the resampling. Other smoothing techniques that may be applicable include additional kernel-based filters like Gaussian, Laplacian or median kernel filters, or low-pass Fourier domain techniques like Butterworth, Chebyshev or Bessel filters.

FIG. 13A shows an enhanced noise surface file associated with the noise surface file of FIG. 12A. In some embodiments, the enhanced noise surface file is generated according to the method described in accordance with the flowchart of FIG. 9. As a result of this enhancement, the input image signature is added to the noise. This process enables terrain definition that is visible in the original image to be expressed into the DTM. For example, terrain break and drain lines that might not be well defined in the DTM as in the input image can be accentuated through this process. Additional terrain characteristics such as texture can also be enhanced in the DTM through this process.

FIG. 13B shows the enhanced DTM (at a output resolution of 1 m) associated with the input DTM of FIG. 11A. FIG. 13B shows the final output of the process, i.e., the enhanced DTM having a 1 m resolution. One aspect of the DTM enhancement process is that the disclosed process approximates the noise characteristics of the sensor type used to produce the DTM (e.g. IFSAR, LiDAR, stereo photo etc.) and adds real terrain signatures from the input image to restore the terrain data to the full definition as present in the image.

Figure 14:
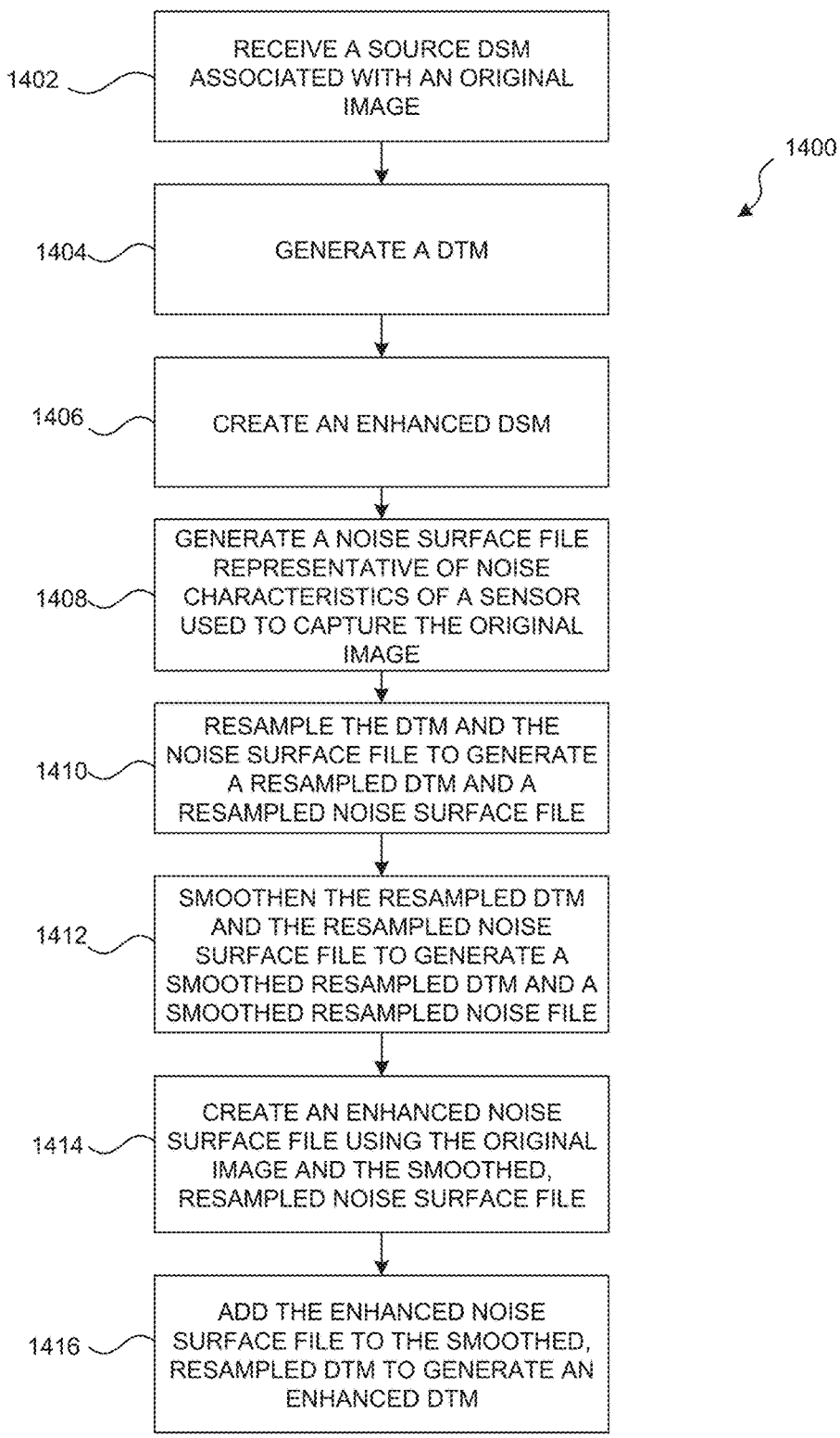
FIG. 14 shows steps of a flowchart associated with enhancing the resolution of an input DTM.

FIG. 14 shows steps of a flowchart of a process 1400 associated with enhancing the resolution of an input DTM. At step 1402, the process receives a source DSM associated with an original (input) image. At step 1404, the process generates a DTM based on removing one or more surface features from the original image. At step 1406, the process creates an enhanced DSM (e.g., using the method described in FIG. 9) associated with the original image. At step 1408, the process generates a noise surface file representative of noise characteristics of a sensor used to capture the original image. At step 1410, the process resamples the DTM and the noise surface file to generate a resampled DTM and a resampled noise surface file, having a resolution of the target (output) DTM. At step 1412, the process smoothens the resampled DTM and the resampled noise surface file to generate a smoothed resampled DTM and a smoothed resampled noise file. In some embodiments, the smoothing can be performed using a filter corresponding to the noise characteristics of the sensor associated with the original image. At step 1414, the process creates an enhanced noise surface file using the original image and the smoothed, resampled noise surface file. At step 1416, the process adds the enhanced noise surface file to the smoothed, resampled DTM to generate an enhanced DTM with a resolution greater than the DTM. The process terminates thereafter.

Figure 15:
FIG. 15 shows a representative obstruction mask for blending the enhanced DSM of FIG. 10C into the enhanced DTM of FIG. 13B.

FIG. 15 shows a representative obstruction mask for blending the enhanced DSM of FIG. 10C into the enhanced DTM of FIG. 13b. The darker portions of the mask in FIG. 16 correspond to the unobstructed or "bald" portions of the image whereas the lighter portions correspond to the obstructed portions of the image. The obstruction mask is a file that separates obstructed areas from unobstructed areas of the image. Obstructed areas are portions of the image including above-the-ground features such as vegetation, urban development, man-made structures, crops, etc. In some implementations, the obstruction mask can be a raster file with the same dimensions as the input DTM with each pixel in the obstruction mask individually classified as obstructed or unobstructed.

Figure 16:
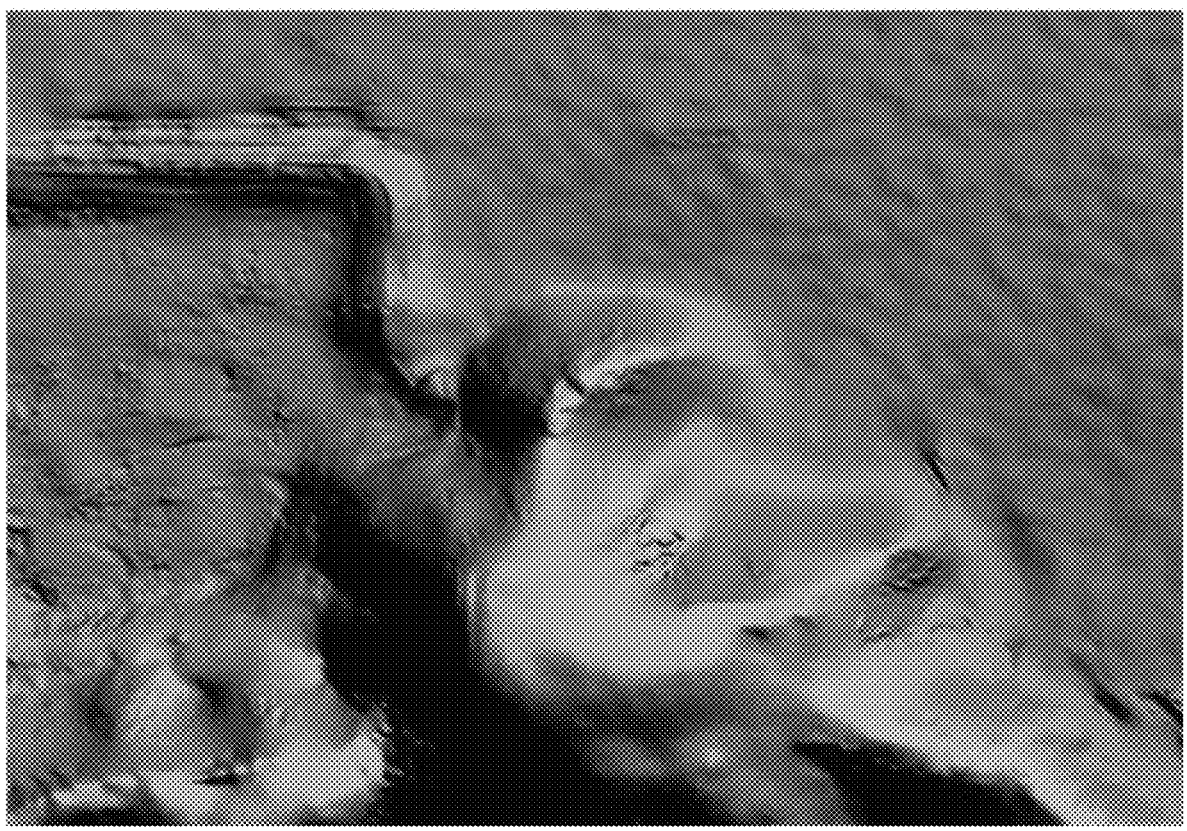
FIG. 16 shows the outcome of applying an obstruction mask to the enhanced DTM of FIG. 13B.

FIG. 16 shows the outcome of applying an obstruction mask to the enhanced DTM of FIG. 13B. The blending of the enhanced DSM into the enhanced (output) DTM can be done using digital elevation model (DEM) fusion blending over an area within the bald areas. This blending size can be flexible. In the example shown in FIG. 16, the size of the blending area used is 20 pixels.

Figure 17:
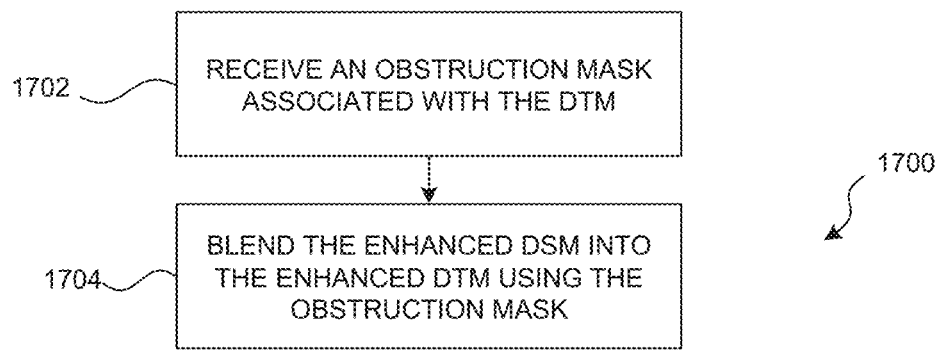
FIG. 17 shows steps of a flowchart associated with applying an obstruction mask.

FIG. 17 shows steps of a flowchart of a process associated with applying an obstruction mask. The process of applying an obstruction mask is optional and can be considered as an add-on feature to the high resolution DTM generated using the steps disclosed in FIG. 14. At step 1702, the process receives an obstruction mask associated with the source DSM. At step 1704, the process blends the enhanced DSM into the enhanced DTM using the obstruction mask.

Figure 18:
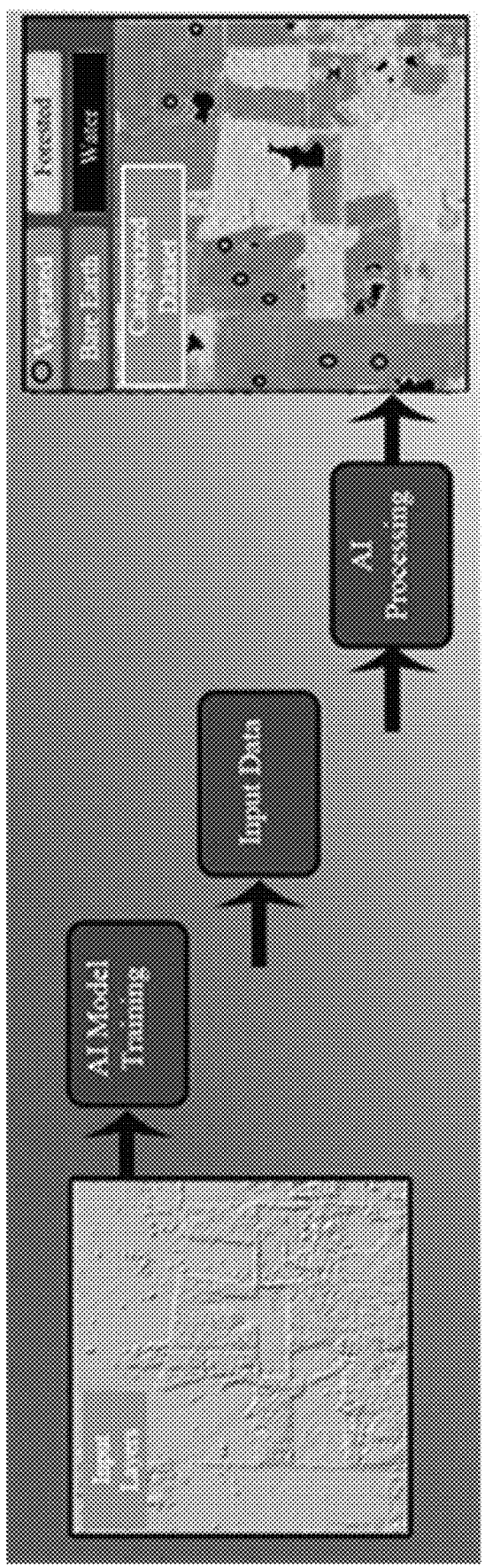
FIG. 18 shows a block diagram of steps involved in segmentation of a digital elevation model (DEM).

FIG. 18 shows a block diagram of steps involved in segmentation of a digital elevation model (DEM). In some embodiments, these steps are additional (optional) steps that are commonly performed during the DEM finishing process (i.e. the process of refining a DSM and creating/refining a DTM from that DSM). Categorical segmentation of a DEM into key land cover types (such as bare earth, vegetated, water and cultural features) can be a first step in DEM finishing. For example, the segmentation can help with ensuring the use of appropriate tools for hydro enforcement and removal of vegetation and cultural features for DTM generation.

In some embodiments (e.g., as shown in FIG. 18), DEM finishing involves applying machine learning (ML) methods for data categorization, resulting in greater efficiency in the DEM finishing process. For example, pixel-wise classification can be achieved using a U-net classifier as part of a model. One advantage of the model is that it maintains the input image resolution while learning the properties of the classes of interest. U-net classifiers typically use convolutional layers (common to several image-based neural networks) to learn regional characteristics of an input image. The regional characteristics of a group of pixels can be more reliable for categorical classification than individual pixels because they take contextual information into account. U-net classifiers typically combine up-sampled contextual information, from the convolutional layers, with higher-resolution layers that skip the convolutional layers at multiple stages in the process. The depth and breadth of the information from a U-net classifier produces high quality image segmentations.

Figure 19B:
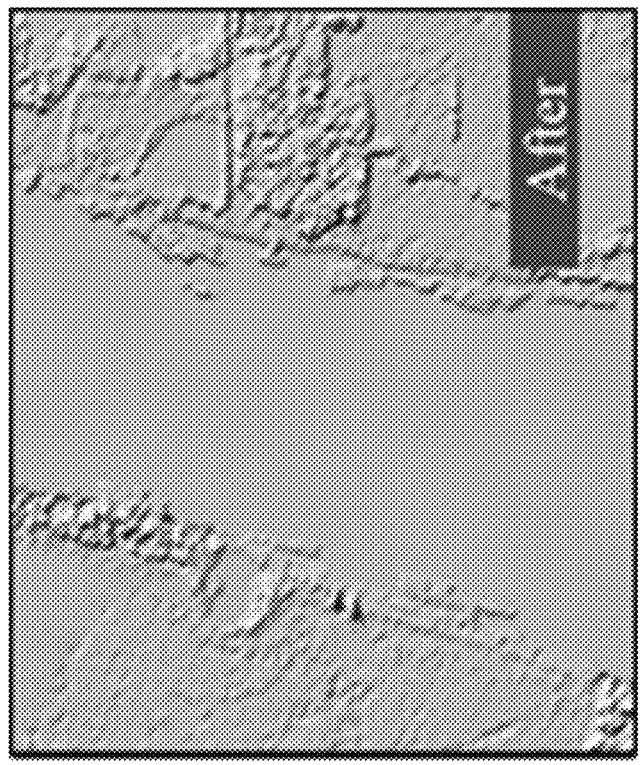
FIGS. 19A, 19B show examples of hydrology features before and after, as part of a DEM finishing process.
Figure 19A:
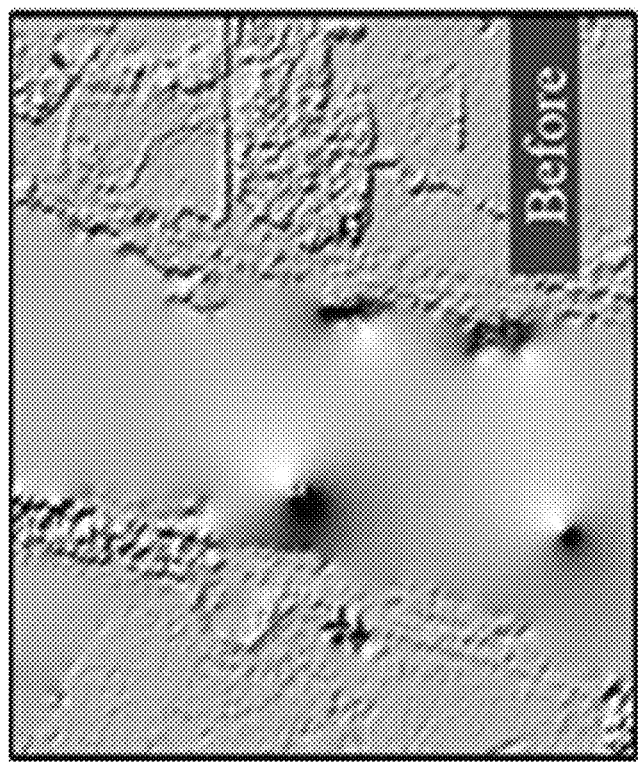

FIGS. 19A, 19B show examples of hydrology features before and after, as part of a DEM finishing process. Enforcement of hydrology as part of the DEM finishing process can be beneficial because sensors typically are subjected to produce weak or poor returns from capturing images of waterbodies. As shown in FIG. 19A, this can result in void or interpolated areas and irregular patterns that adversely affect models, applications and analytics derived from the data. Consequently, hydro-enforced elevation content can be beneficial, as shown in FIG. 19B.

Figure 20A:
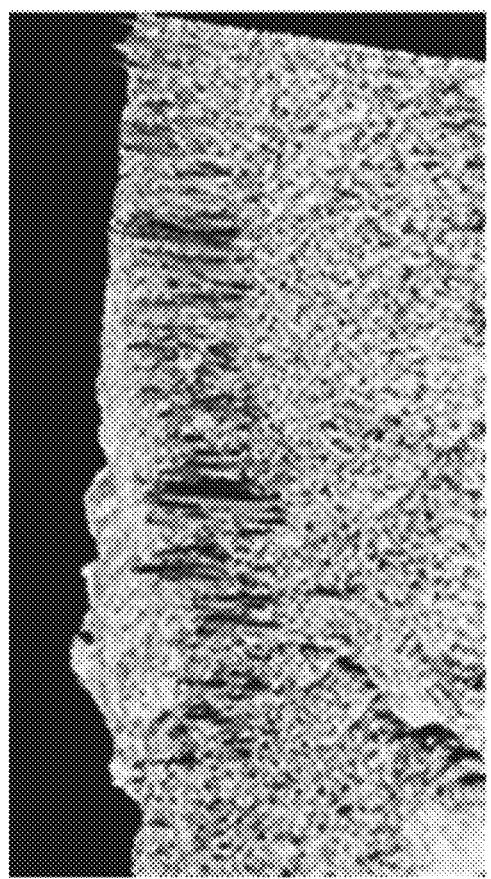
FIGS. 20A, 20B show examples of source elevation content in a DEM before and after, as part of a DEM finishing process.
Figure 20B:
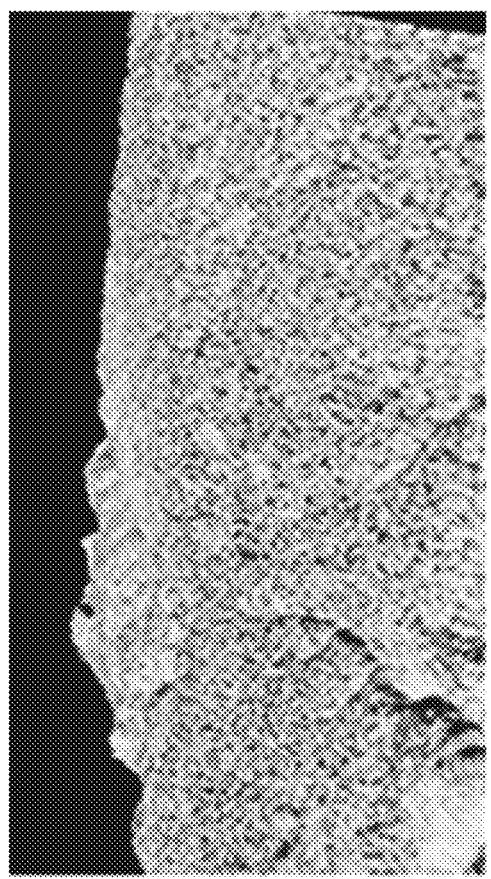

FIGS. 20A, 20B show examples of source elevation content in a DEM before and after, as part of a DEM finishing process. In some instances, source elevation datasets can include spike and well artifacts, as shown in FIG. 20A. As part of the DEM finishing process, these issues can be corrected, as shown in FIG. 20B. The correction involves an ancillary fusion process using an ancillary data source of high quality. The fusion process includes creating a smoothed version of the dataset using a kernel filter such as an averaging filter or a Gaussian filter. The kernel size of the filter can be selected to be large enough to remove any large spikes in the dataset. (Sizes of the spikes and artifacts may vary depending on the data source.) A difference surface is then created by subtracting the original dataset from the smoothed dataset. Finally, a mask is created by thresholding the difference surface, such that any differences greater than a specified threshold value are included in the mask. The threshold value may be specified differently depending on the data source and the extent of spikes present. Any areas identified by the mask are considered blunders, which can be corrected using an ancillary fusion process.

Figure 21B:
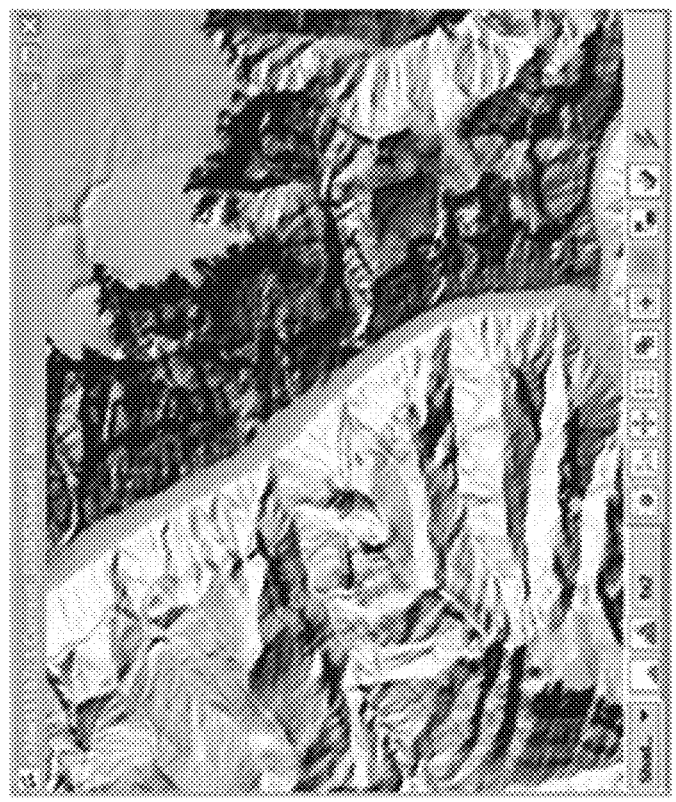
FIGS. 21A, 21B show examples of filling void areas as part of a DEM finishing process.
Figure 21A:
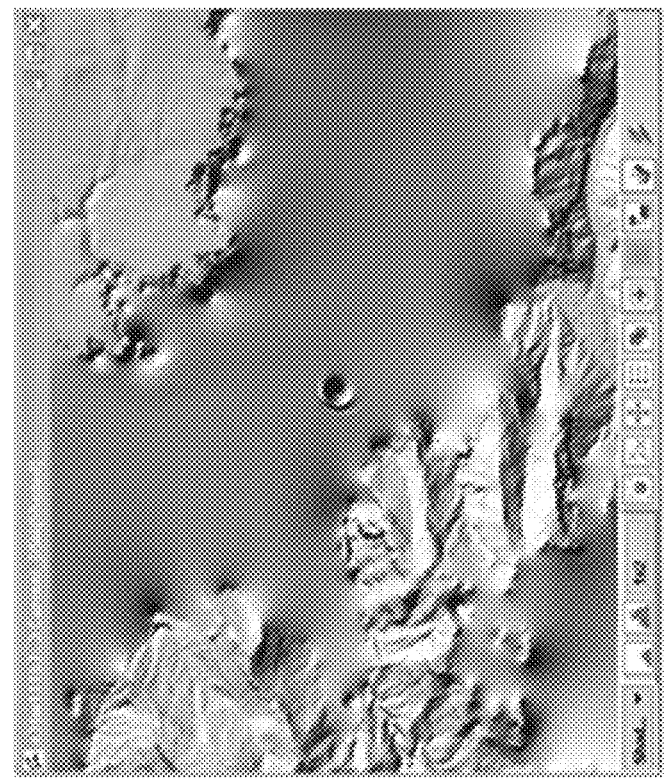

FIGS. 21A, 21B show examples of filling void areas as part of a DEM finishing process. For example, FIG. 21B shows before a void fill and FIG. 21B shows after a void fill.

Figure 22A:
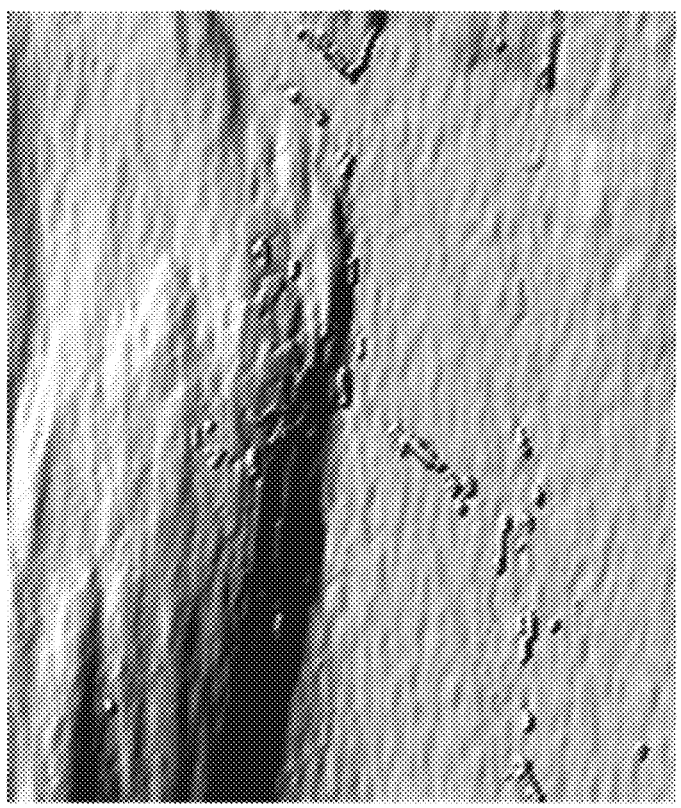
FIGS. 22A, 22B show examples of fixing data artifacts as part of a DEM finishing process.
Figure 22B:

FIGS. 22A, 22B show examples of fixing data artifacts as part of a DEM finishing process. For example, FIG. 22A shows before fixing data artifacts and FIG. 22B shows after fixing data artifacts.

Figure 23B:
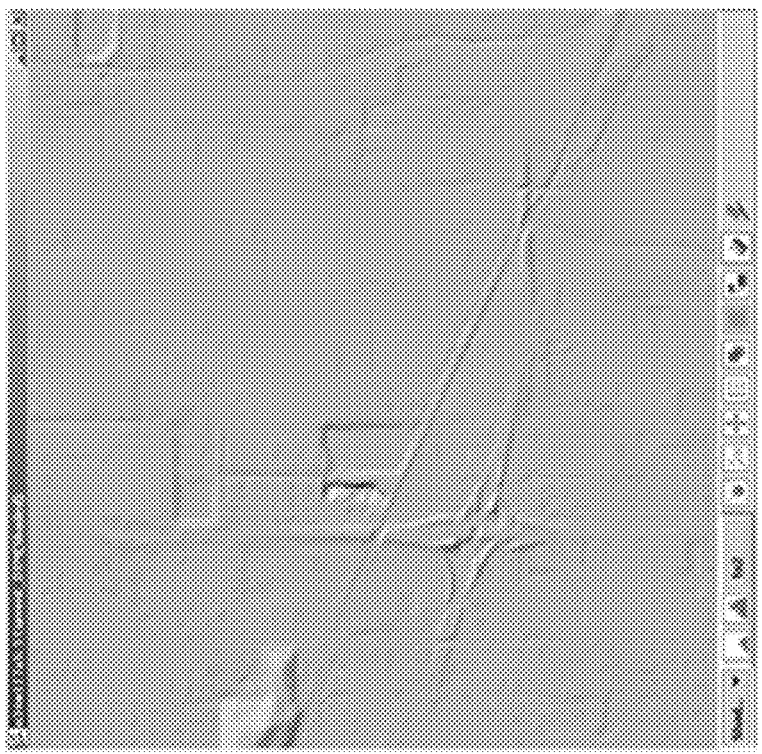
FIGS. 23A, 23B show examples of removing vegetation and buildings.
Figure 23A:
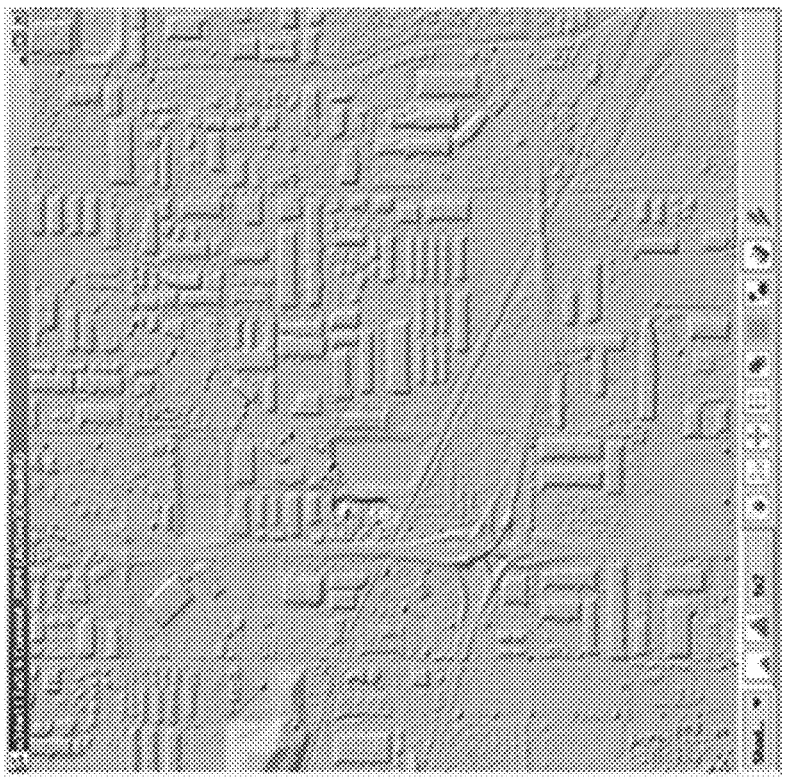

FIGS. 23A, 23B show examples of removing vegetation and buildings. The removal involves transforming a DSM into a DTM. For example, FIG. 23A shows before removal and FIG. 23B shows after removal.

Figure 24:
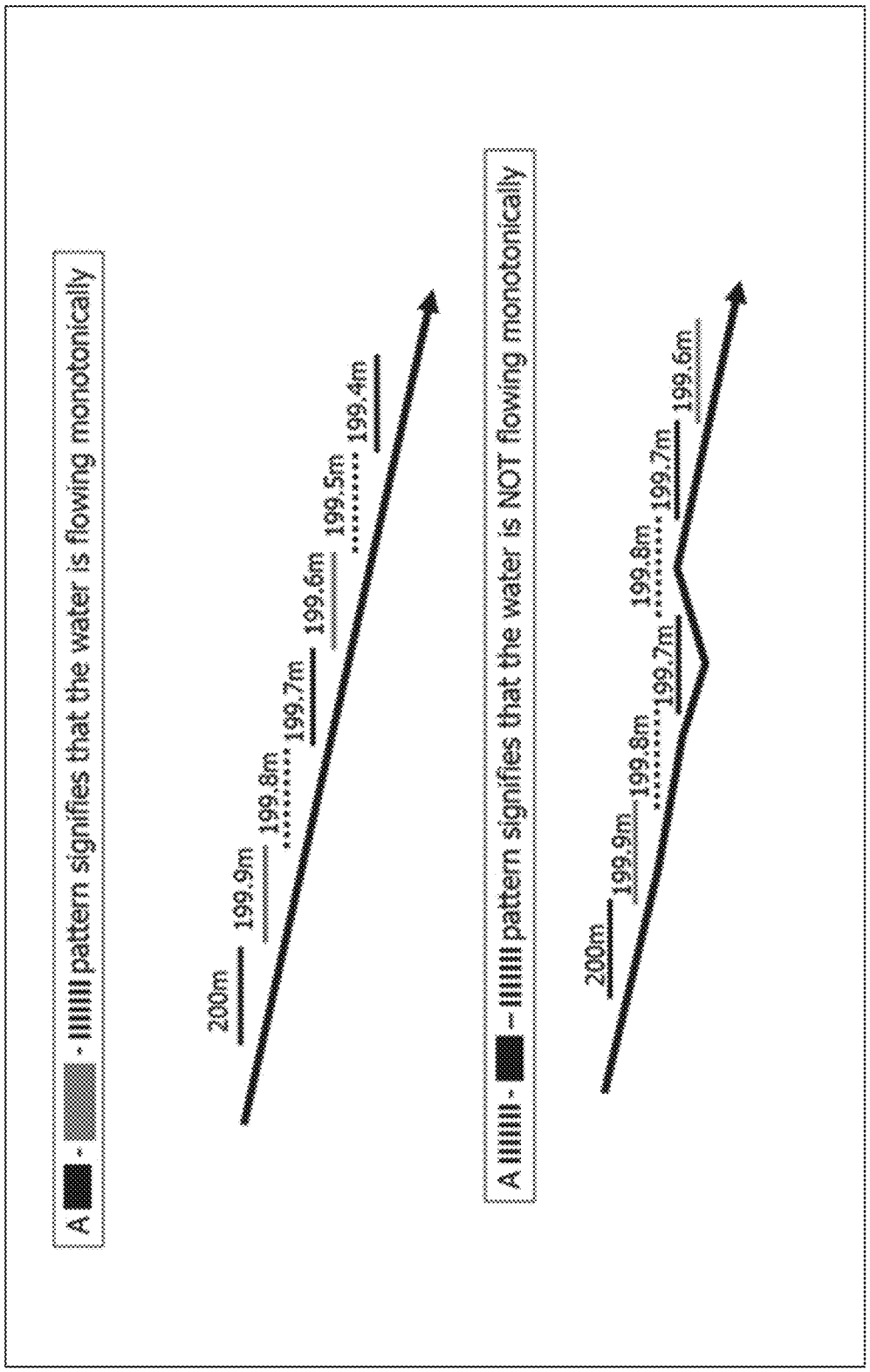
FIG. 24 illustrates monotonicity.

FIG. 24 illustrates monotonicity. Monotonicity is a feature associated with waterbodies such as streams and rivers. Monotonicity refers to the direction of flow for a moving waterbody. The DEM finishing process involves enforcing monotonicity in the DEM. As discussed in FIG. 24, monotonic (and non-monotonic water flows) can be identified by the presence of a pattern in the DEM.

Figure 25B:
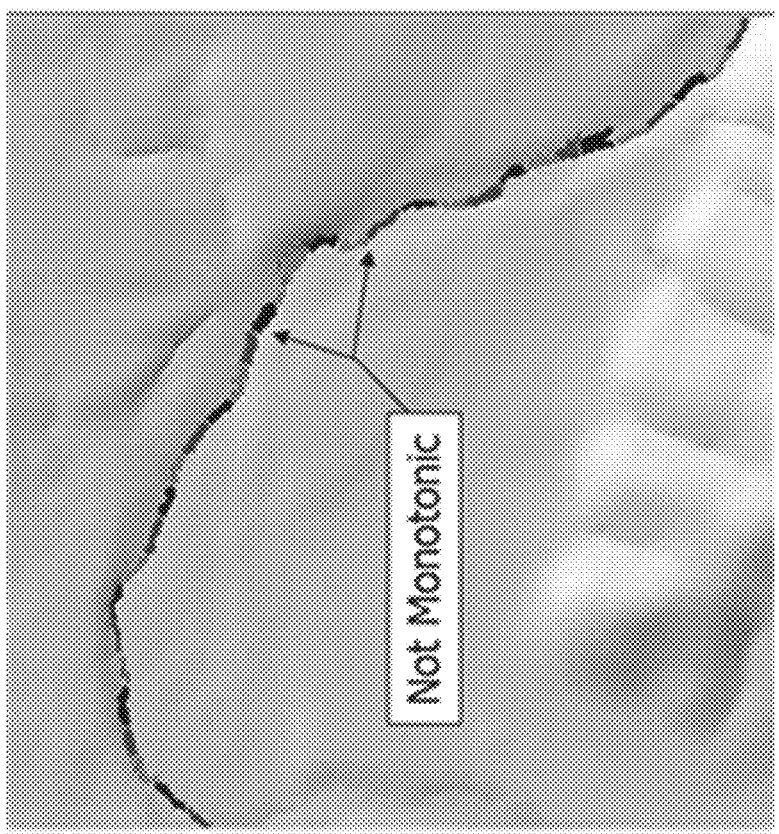
FIGS. 25A, 25B show examples of monotonic and non-monotonic water flow.
Figure 25A:
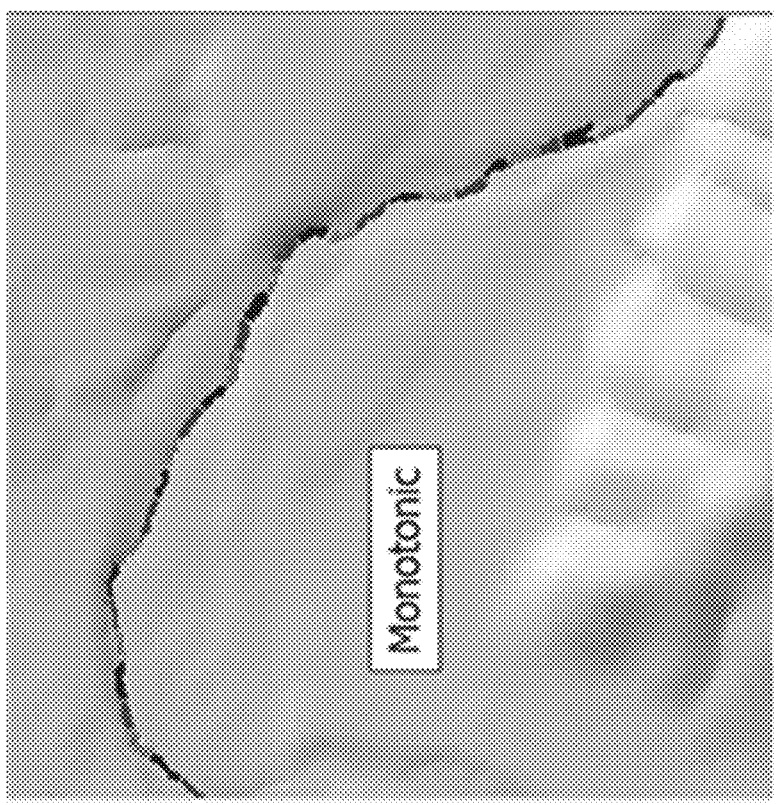

FIGS. 25A, 25B show examples of monotonic and non-monotonic water flow, based on the presence or lack of a pattern in the DEM.

Some of the embodiments described herein are described in the general context of methods or processes, which may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Therefore, the computer-readable media may include a non-transitory storage media. Generally, program modules may include routines, programs, objects, components, data structures, etc. that perform particular tasks or implement particular abstract data types. Computer- or processor-executable instructions, associated data structures, and program modules represent examples of program code for executing steps of the methods disclosed herein. The particular sequence of such executable instructions or associated data structures represents examples of corresponding acts for implementing the functions described in such steps or processes.

Some of the disclosed embodiments may be implemented as devices or modules using hardware circuits, software, or combinations thereof. For example, a hardware circuit implementation may include discrete analog and/or digital components that are, for example, integrated as part of a printed circuit board. Alternatively, or additionally, the disclosed components or modules may be implemented as an Application Specific Integrated Circuit (ASIC) and/or as a Field Programmable Gate Array (FPGA) device. Some implementations may additionally or alternatively include a digital signal processor (DSP) that is a specialized microprocessor with an architecture optimized for the operational needs of digital signal processing associated with the disclosed functionalities of this application. Similarly, the various components or sub-components within each module may be implemented in software, hardware or firmware. The connectivity between the modules and/or components within the modules may be provided using any one of the connectivity methods and media that is known in the art, including, but not limited to, communications over the Internet, wired, or wireless networks using the appropriate protocols.

The foregoing description of embodiments has been presented for purposes of illustration and description. The foregoing description is not intended to be exhaustive or to limit embodiments of the present invention(s) to the precise form disclosed, and modifications and variations are possible in light of the above teachings or may be acquired from practice of various embodiments. The embodiments discussed herein were chosen and described in order to explain the principles and the nature of various embodiments and its practical application to enable one skilled in the art to utilize the present invention(s) in various embodiments and with various modifications as are suited to the particular use contemplated. The features of the embodiments described herein may be combined in all possible combinations of methods, apparatus, modules, systems, and computer program products.

The invention claimed is:

1. A computer-implemented method comprising:
    smoothing a resampled digital terrain model (DTM) and a resampled noise surface file using a filter representative of noise characteristics of a sensor used to capture an original image for generating a smoothed resampled DTM and a smoothed resampled noise surface file;
    creating an enhanced noise surface file using the original image and the smoothed, resampled noise surface file; and
    adding the enhanced noise surface file to the smoothed, resampled DTM to generate an enhanced DTM with a resolution greater than a DTM corresponding to the resampled DTM.

2. The computer-implemented method of claim 1, wherein the resampled DTM or the resampled noise surface file is based at least on: bilinear resampling, bicubic resampling, nearest neighbor resampling, natural neighbor resampling, kriging resampling, box average resampling, or box median resampling.

3. The computer-implemented method of claim 1, further comprising:
    receiving a source digital surface model (DSM) associated with the original image to generate a resampled DSM;
    resampling the source DSM for one or more pixels in the original image;
    creating a difference model based on subtracting the resampled DTM from the resampled DSM;
    generating a map based on correlating at least one pixel in the difference model to a group of pixels in the original image; and
    constructing an enhanced DSM by manipulating one or more pixels in the original image based on the map.

4. The computer-implemented method of claim 1, wherein creating the enhanced noise surface file includes:
    receiving the smoothed resampled noise surface file;
    creating a difference model based on subtracting the smoothed resampled noise surface file from the resampled noise surface file;
    generating a map based on correlating at least one pixel in the difference model to a group of pixels in the noise surface file; and
    constructing the enhanced noise surface file by manipulating one or more pixels in the noise surface file based on the map.

5. The computer-implemented method of claim 1, further comprising:
    receiving an obstruction mask associated with the DTM for distinguishing between obstructed areas and unobstructed surface areas of the original image; and
    blending the enhanced DSM into the enhanced DTM using the obstruction mask.

6. The computer-implemented method of claim 1, wherein each pixel in the resampled DTM or the resampled noise surface file is associated with a corresponding pixel in the original image.

7. The computer-implemented method of claim 1, wherein a footprint of the noise surface file corresponds to a footprint of a target digital model of the original image such that the resampled noise surface file has a resolution of the target digital model of the original image.

8. The computer-implemented method of claim 3, further comprising:
    upon determining that the original image is not in a grayscale format, converting the original image to the grayscale format for extracting grayscale values of one or more pixels in the original image.

9. The computer-implemented method of claim 8, further comprising:
    manipulating the grayscale values based on the map; and
    generating a regression model from the map.

10. The computer-implemented method of claim 9, wherein the regression model corresponds to a linear model.

11. The computer-implemented method of claim 9, wherein the regression model corresponds to a non-linear model.

12. The computer-implemented method of claim 4, wherein a neighborhood adjacent to each pixel in the difference model is a kernel of a predetermined size.

13. The computer-implemented method of claim 1, wherein the original image is at least one of: a thermal image, a multi-spectral image, a hyper-spectral image, an optical image, a medical image, a radar image, a weather image, a fused image from multiple types of sensors, a color image, a gray scale image, or a LiDAR intensity image.

14. A non-transitory computer-readable storage medium storing instructions configured to cause at least one computing device to perform a method comprising:
smoothing a resampled digital terrain model (DTM) and a resampled noise surface file using a filter corresponding representative of noise characteristics of a sensor used to capture an original image for generating a smoothed resampled DTM and a smoothed resampled noise surface file;
creating an enhanced noise surface file using the original image and the smoothed, resampled noise surface file; and
adding the enhanced noise surface file to the smoothed, resampled DTM to generate an enhanced DTM with a resolution greater than a DTM corresponding to the resampled DTM.

15. The computer-readable storage medium of claim 14, wherein the resampled DTM or the resampled noise surface file is based at least on: bilinear resampling, bicubic resampling, nearest neighbor resampling, natural neighbor resampling, kriging resampling, box average resampling, or box median resampling.

16. The computer-readable storage medium of claim 14, further comprising:
receiving a source digital surface model (DSM) associated with the original image to generate a resampled DSM;
resampling the source DSM for one or more pixels in the original image;
creating a difference model based on subtracting the resampled DTM from the resampled DSM;
generating a map based on correlating at least one pixel in the difference model to a group of pixels in the original image; and
constructing an enhanced DSM by manipulating one or more pixels in the original image based on the map.

17. The computer-readable storage medium of claim 14, wherein creating the enhanced noise surface file includes:
receiving the smoothed resampled noise surface file;
creating a difference model based on subtracting the smoothed resampled noise surface file from the resampled noise surface file;
generating a map based on correlating at least one pixel in the difference model to a group of pixels in the noise surface file; and
constructing the enhanced noise surface file by manipulating one or more pixels in the noise surface file based on the map.

18. The computer-readable storage medium of claim 14, the method further comprising:
receiving an obstruction mask associated with the DTM for distinguishing between obstructed and unobstructed surface areas of the original image; and
blending the enhanced DSM into the enhanced DTM using the obstruction mask.

19. A computer system comprising:
at least one processor and
at least one memory comprising instructions configured to cause the at least one processor to perform a method comprising:
smoothing a resampled digital terrain model (DTM) and a resampled noise surface file using a filter representative of noise characteristics of a sensor used to capture an original image for generating a smoothed resampled DTM and a smoothed resampled noise surface file;
creating an enhanced noise surface file using the original image and the smoothed, resampled noise surface file; and
adding the enhanced noise surface file to the smoothed, resampled DTM to generate an enhanced DTM with a resolution greater than a DTM corresponding to the resampled DTM.

20. The system of claim 19, wherein the resolution of the enhanced DTM is invariant to scale changes in the original image or the noise characteristics of the sensor used to capture the original image.

* * * * *

UNITED STATES PATENT AND TRADEMARK OFFICE
CERTIFICATE OF CORRECTION

PATENT NO. : 10,535,119 B2  
APPLICATION NO. : 16/398027  
DATED : January 14, 2020  
INVENTOR(S) : Mercer et al.

Page 1 of 1

It is certified that error appears in the above-identified patent and that said Letters Patent is hereby corrected as shown below:

On the Title Page

• Item (54), and in the Specification Column 1, Lines 1-2, change Title from "METHOD AND APPARATUS FOR ENHANCING 3D MODEL RESOLUTION" to "METHOD AND APPARATUS FOR ENHANCING RESOLUTIONS OF DIGITAL TERRAIN MODELS".

• On page 2, item (60), in Column 1, in "Related U.S. Application Data", Line 3, delete "62/544,608." and insert -- 62/544,608, filed on Aug. 11, 2017. --, therefor.

Signed and Sealed this  
Twenty-second Day of February, 2022

Drew Hirshfeld  
*Performing the Functions and Duties of the*  
*Under Secretary of Commerce for Intellectual Property and*  
*Director of the United States Patent and Trademark Office*